United States Patent
Chi et al.

(10) Patent No.: US 10,870,629 B2
(45) Date of Patent: Dec. 22, 2020

(54) 18F-LABELLED COMPOUND FOR PROSTATE CANCER DIAGNOSIS, AND USE THEREOF

(71) Applicant: FUTURECHEM CO., LTD., Seoul (KR)

(72) Inventors: Dae Yoon Chi, Seoul (KR); Byoung Se Lee, Seoul (KR); So Young Chu, Seoul (KR); Woon Jung Jung, Seoul (KR); Hyeon Jin Jeong, Seoul (KR); Min Hwan Kim, Seoul (KR); Mi Hyun Kim, Seoul (KR); Kyo Chul Lee, Seoul (KR); Yong Jin Lee, Seoul (KR); Ji Ae Park, Seoul (KR); Ran Ji Yoo, Seoul (KR); Sang Moo Lim, Seoul (KR)

(73) Assignee: FUTURECHEM CO., LTD., Seoul (KR)

( * ) Notice: Subject to any disclaimer, the term of this patent is extended or adjusted under 35 U.S.C. 154(b) by 0 days.

(21) Appl. No.: 16/622,518

(22) PCT Filed: Jun. 18, 2018

(86) PCT No.: PCT/KR2018/006869
§ 371 (c)(1),
(2) Date: Dec. 13, 2019

(87) PCT Pub. No.: WO2018/236115
PCT Pub. Date: Dec. 27, 2018

(65) Prior Publication Data
US 2020/0207724 A1    Jul. 2, 2020

(30) Foreign Application Priority Data

Jun. 19, 2017 (KR) .................. 10-2017-0077570
Jun. 18, 2018 (KR) .................. 10-2018-0069590

(51) Int. Cl.
*C07D 249/04* (2006.01)
*A61K 51/04* (2006.01)

(52) U.S. Cl.
CPC ............ *C07D 249/04* (2013.01); *A61K 51/04* (2013.01)

(58) Field of Classification Search
CPC .............................. C07D 249/04; A61K 51/04
See application file for complete search history.

(56) References Cited

U.S. PATENT DOCUMENTS

2013/0034494 A1    2/2013  Babich et al. ............... 424/1.65

FOREIGN PATENT DOCUMENTS

| KR | 10-2011-0038725 | 4/2011 |
| KR | 10-2015-0115797 | 10/2015 |
| KR | 10-2016-0085769 | 7/2016 |
| WO | 2010/014933 | 2/2010 |
| WO | 2013/028664 | 2/2013 |
| WO | 2014/110372 | 7/2014 |
| WO | 2015/071288 | 5/2015 |
| WO | 2017/027870 | 2/2017 |
| WO | 2018/005625 | 1/2018 |

OTHER PUBLICATIONS

Chen et al. "A [18F]Fluoroethyl Triazol Substituted PSMA Inhibitor Exhibiting Rapid Normal Organ Clearance" Bioconjugate Chemistry 2016 pp. 1-25.
International Search Report and Written Opinion in PCT/KR2018/006869 dated Sep. 21, 2018 with English Language translation.

*Primary Examiner* — Shawquia Jackson
(74) *Attorney, Agent, or Firm* — Licata & Tyrrell P.C.

(57) ABSTRACT

The present invention relates to an 18F-labelled compound, and a use thereof. The compound selectively binds to a prostate-specific membrane antigen (PSMA), and enables the acquisition of clear prostate cancer images in a short time when used in positron emission tomography (PET).

9 Claims, 9 Drawing Sheets

18F-LABELLED COMPOUND FOR PROSTATE CANCER DIAGNOSIS, AND USE THEREOF

This patent application is the National Stage of International Application No. PCT/KR2018/006869 filed Jun. 18, 2018 and claims the benefit of priority from Korean Application No. 10-2018-0069590, filed Jun. 18, 2018, and Korean Application No. 10-2017-0077570, filed Jun. 19, 2017, each of which are herein incorporated by reference in their entirety.

BACKGROUND OF THE INVENTION

1. Field of the Invention

The present invention relates to an $^{18}$F-labelled compound for prostate cancer diagnosis, and a use thereof.

2. Description of the Related Art

Prostate cancer is the leading cause of death among male cancers in the United States, fifth in Korea and second in the world. Prostate cancer usually develops in men over 50, but the number of patients increases rapidly with age. It usually progresses 25 slowly, but when it develops into a malignant metastasis, it is extremely difficult to treat. The metastasis usually begins to the lymph nodes, pelvic bones, vertebrae and bladder around prostate cancer and gradually spreads throughout the body.

Prostate-specific antigen test (PSA test) and digital rectal examination are currently used primarily for prostate cancer diagnosis, and transrectal ultrasonography, CT, MRI and whole body bone scan (WBBS) imaging are also used. Biopsies for prostate cancer diagnosis are also being conducted. However, in most cases the diagnostic accuracy is low and early diagnosis of the disease is difficult. In addition, it is difficult to determine metastasis and difficult to distinguish from benign diseases such as prostate hyperplasia and prostatitis.

PET (Positron Emission Tomography) is a human imaging method using molecular probes targeting disease-specific metabolism or protein. This method has advantages in early diagnosis, evaluation of treatment and confirmation of metastasis/recurrence by observing biochemical changes in the early stage of the disease by using a short half-life radioisotope.

[$^{18}$F] FDG is a representative PET radiopharmaceutical used for cancer diagnosis because it can observe the enhanced glucose metabolism of cancer cells. One example of such a technique is disclosed in Patent Reference 1 below. However, in the case of prostate cancer, the intake of [$^{18}$F] FDG is not high so that it is difficult to use for prostate cancer diagnosis. In addition, compounds such as [$^{18}$F] fluorocholine, [$^{11}$C] acetate, and [$^{18}$F] FACBC have been applied for prostate cancer diagnosis. However, when using them, the accuracy of diagnosis is not high, and the small sized prostate cancer metastasized is difficult to observe.

Prostate-Specific Membrane Antigen (PSMA) is a protein that is specifically overexpressed in prostate cancer, and it is known that the urea-based dipeptide compound of glutamic acid-Urea-lysine (GUL) binds thereto very selectively. Several compounds labeled with GUL-based radioisotopes have been developed as prostate cancer-specific diagnostic drugs. Among them, $^{18}$F-DCFPyL is an $^{18}$F isotope-labeled GUL compound and is evaluated as one of the best PET tracers for prostate cancer diagnosis. The said $^{18}$F-DCFPyL has a relatively low lipophilic property compared to the previously developed compound ($^{18}$F-DCFBzL), so that it has a low non-specific binding property in vivo and is quickly removed through the kidney.

Recently, a compound called $^{18}$F-YC88 was further developed. It is a compound having a lower lipophilic property than the $^{18}$F-DCFPyL compound, which is characterized by reducing non-specific binding further and is rapidly removed. However, this compound has a problem that the binding force to the PSMA protein is reduced by about 10 times compared to $^{18}$F-DCFPyL, and the prostate cancer signal is greatly reduced over the time.

PRIOR ART REFERENCE

Korean Patent Publication No. 10-2016-0085769,
Korean Patent Publication No. 10-2011-0038725

SUMMARY OF THE INVENTION

It is an object of the present invention to provide an $^{18}$F-labeled compound capable of accurate diagnosis of prostate cancer and a use thereof.

The object of the present invention is not limited to the above-mentioned object. The object of the present invention will become more apparent from the following description, and will be realized by the means described in the claims and the combinations thereof.

A compound according to an embodiment of the present invention is represented by the following formula 1.

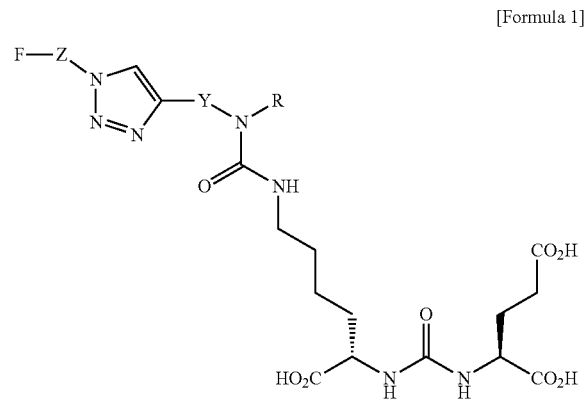

[Formula 1]

In formula 1, Y is $C_1$-$C_5$ alkylene; and Z is —$CH_2$—($CH_2$—O—$CH_2$)$_n$—$CH_2$—, wherein n is an integer of 0 to 5; R is hydrogen or $C_1$-$C_2$ alkyl having an substituent, wherein the substituent is $C_6$-$C_{12}$ aryl or $C_4$-$C_{10}$ heteroaryl containing one or more elements selected from the group consisting of O, S and N; and F can be $^{18}$F or $^{19}$F.

Y is $C_1$-$C_2$ alkylene, and F can be $^{18}$F.

A compound according to another embodiment of the present invention is represented by the following formula 11.

[Formula 11]

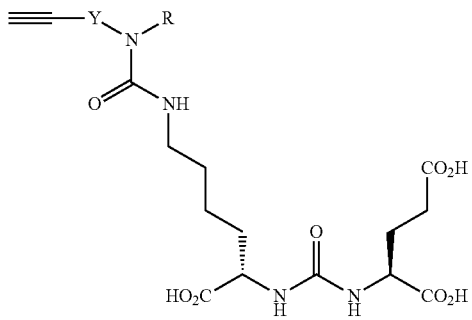

In formula 11, Y is $C_1$-$C_5$ alkylene; and R is hydrogen or $C_1$-$C_2$ alkyl having an substituent, wherein the substituent is $C_6$-$C_{12}$ aryl or $C_4$-$C_{10}$ heteroaryl containing one or more elements selected from the group consisting of O, S and N.

Y can be $C_1$-$C_2$ alkylene.

A pharmaceutical composition for treating or diagnosing prostate cancer according to another embodiment of the present invention comprises a compound of formula 1 or a pharmaceutically acceptable salt thereof.

A radiopharmaceutical for imaging diagnosis of prostate cancer according to another embodiment of the present invention comprises a compound of formula 1 or a pharmaceutically acceptable salt thereof.

The imaging diagnosis can include positron emission tomography (PET).

Advantageous Effect

According to an embodiment of the present invention, the compound of formula 1 to which $^{18}$F is bound has high hydrophilicity, excellent in vivo pharmacokinetic properties and low non-specific binding, so that clear positron emission tomography (PET) images can be obtained in a short time.

DESCRIPTION OF THE PREFERRED EMBODIMENTS

Figure 1A:
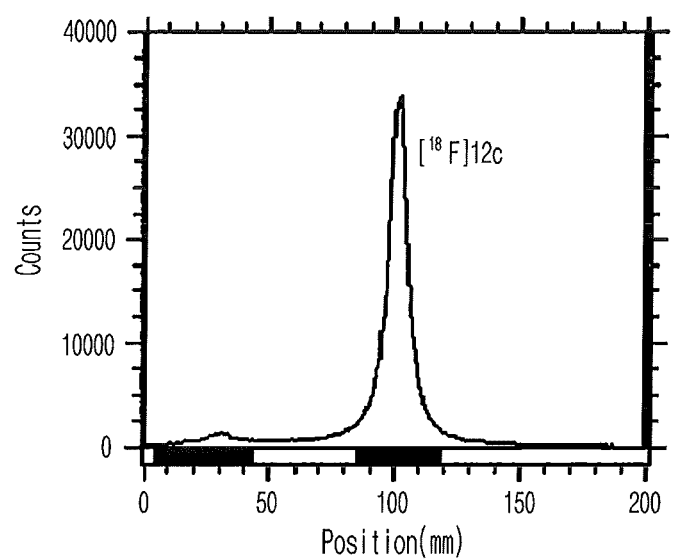
FIGS. 1A and 1B are diagrams illustrating the results of Radio-TLC according to the preparation step of the compound [$^{18}$F]1-6.

The above objects, other objects, features and advantages of the present invention are readily understood through the following preferred examples associated with the accompanying drawings. However, the present invention is not limited to the examples described herein and can be embodied in other forms. Rather, the examples introduced herein are provided so that the disclosure can be made thorough and complete, and to fully transfer the spirit of the present invention to those skilled in the art.

Hereinafter, a compound represented by formula 1 of the present invention is described in detail.

The present invention includes a compound represented by the following formula 1.

[Formula 1]

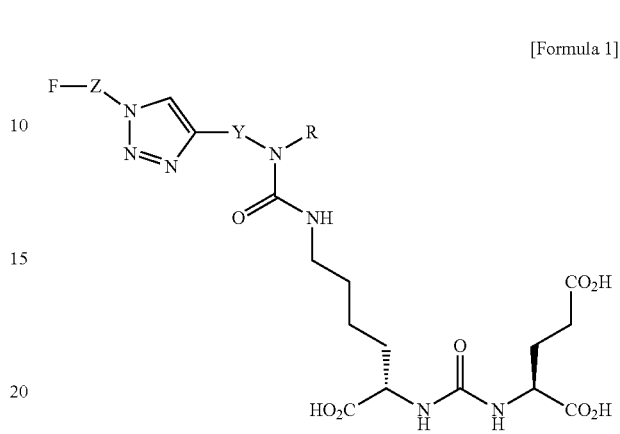

In formula 1,
Y is $C_1$-$C_5$ alkylene;
Z is —$CH_2$—($CH_2$—O—$CH_2$)$_n$—$CH_2$—, wherein n is an integer of 0 to 5;
R is hydrogen or $C_1$-$C_2$ alkyl having an substituent, wherein the substituent is $C_6$-$C_{12}$ aryl or $C_4$-$C_{10}$ heteroaryl containing one or more elements selected from the group consisting of O, S and N; and
F can be $^{18}$F or $^{19}$F.
More specifically, Y is $C_1$-$C_2$ alkylene;
Z is —$CH_2$—($CH_2$—O—$CH_2$)$_n$—$CH_2$—, wherein n is an integer of 0 to 5;
R is hydrogen or $C_1$-$C_2$ alkyl having an substituent, wherein the substituent is $C_6$-$C_{12}$ aryl or $C_4$-$C_{10}$ heteroaryl containing one or more elements selected from the group consisting of O, S and N; and
F can be $^{18}$F.

Ligands of formula 1 of the present invention can be additionally bound to PSMA proteins via lipophilic bonds because they can be structurally bound to aromatic aryl groups. In addition, the triazole group in the side chain to which $^{18}$F is bound can increase the polarity of the compound to reduce non-specific bindings in vivo.

Such a compound labeled with fluorine-18 of the present invention can have excellent binding capacity to PSMA proteins and excellent pharmacokinetic properties simultaneously.

The present invention provide a pharmaceutical composition for treating or diagnosing prostate cancer comprising a compound of formula 1 or a pharmaceutically acceptable salt thereof as an active ingredient.

The present invention also provides a use of a diagnostic radiopharmaceutical to a subject in need of therapeutic monitoring or imaging diagnosis of prostate cancer. Such a radiopharmaceutical for imaging diagnosis can include a compound of formula 1 or a pharmaceutically acceptable salt thereof as an active ingredient. Herein, the imaging diagnosis can include magnetic resonance imaging (MRI) or positron emission tomography (PET), and preferably can be performed using positron emission tomography (PET).

In the compound described above, radioligands are ingested in the prostate cancer tissues expressing PSMA and can be removed in other organs, so that PET images can be obtained clearly in a short time.

Hereinafter, a compound represented by formula 11 of the present invention is described in detail.

The present invention includes a compound represented by the following formula 11.

[Formula 11]

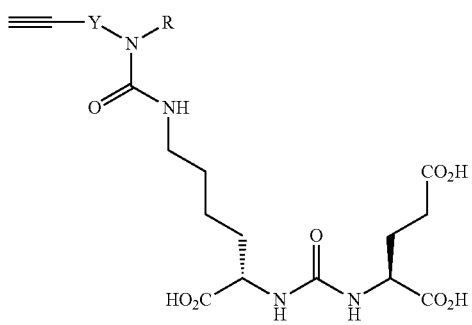

In formula 11,

Y is $C_1$-$C_5$ alkylene; and

R is hydrogen or $C_1$-$C_2$ alkyl having a substituent, wherein the substituent is $C_6$-$C_{12}$ aryl or $C_4$-$C_{10}$ heteroaryl containing one or more elements selected from the group consisting of O, S and N.

More specifically, Y is $C_1$-$C_2$ alkylene; and

R is hydrogen or $C_1$-$C_2$ alkyl having a substituent, wherein the substituent is $C_6$-$C_{12}$ aryl or $C_4$-$C_{10}$ heteroaryl containing one or more elements selected from the group consisting of O, S and N.

Example 1. Preparation of N-Propazyl Amine Derivatives

A schematic reaction process of the present invention is shown in reaction formula 1 below.

[Reaction Formula 1]

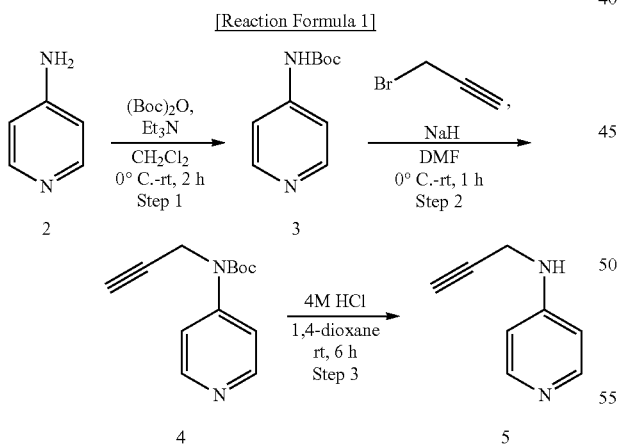

Example 1-1. Preparation of Compound 3 (Step 1)

4-Aminopyridine (2, 9.0 g, 96 mmol) was dissolved in dichloromethane (400 mL), to which (Boc)$_2$O (25.0 g, 110 mmol) was added at 0° C. Triethylamine (20.0 mL, 140 mmol) was slowly added thereto, followed by stirring at room temperature for 2 hours. Water was added thereto and the organic compound was extracted using dichloromethane three times. The collected organic solvent was dried over anhydrous sodium sulfate, concentrated under reduced pressure and purified by column chromatography (7% methanol/dichloromethane). As a result, the compound 3 was obtained as a white solid (18.0 g, 97%).

$^1$H NMR (400 MHz, CDCl$_3$) δ1.53 (s, 9H), 7.29 (brs, 1H), 7.34 (dd, J=4.8, 1.6 Hz, 2H), 8.44 (dd, J=4.8, 1.6 Hz, 2H); $^{13}$C NMR (100 MHz, CDCl$_3$) 528.2, 81.6, 112.3, 145.8, 150.4, 152.0; MS (ESI) m/z 193 [M−H]$^-$ Example 1-2. Preparation of Compound 4 (Step 2)

The compound 3 (18.0 g, 93 mmol) synthesized in step 1 above was dissolved in dimethylformamide (DMF, 400 mL), to which sodium hydride (7.4 g, 900 mmol) was added at 0° C. Propazyl bromide was slowly added thereto, followed by stirring at room temperature for 2 hours. Methanol (50 ml) was added thereto at 0° C., followed by stirring for 30 minutes. Water was added thereto and the organic compound was extracted using ethyl acetate three times. The collected organic solvent was washed with ammonium chloride aqueous solution three times, dried over anhydrous sodium sulfate, concentrated under reduced pressure and purified by column chromatography (5% methanol/dichloromethane). As a result, the compound 4 was obtained as a light yellow solid (13.4 g, 62%).

$^1$H NMR (400 MHz, CDCl$_3$) δ1.53 (s, 9H), 2.31 (t, J=2.6 Hz, 1H), 4.43 (d, J=2.4 Hz, 2H), 7.38 (d, J=5.2 Hz, 2H), 8.54 (m, 2H); $^{13}$C NMR (100 MHz, CDCl$_3$) δ28.1, 38.5, 72.4, 79.1, 82.7, 118.0, 149.2, 150.2, 152.6; MS (ESI) m/z 233 [M+H]$^+$

Example 1-3. Preparation of Compound 5 (Step 3)

Dioxane (75 mL) containing 4N HCl was added to the compound 4 (13.0 g, 56 mmol) synthesized in step 2 above, followed by stirring at room temperature for 6 hours. 2N sodium hydroxide aqueous solution (500 ml) was added thereto and the organic compound was extracted using dichloromethane three times. The collected organic solvent was dried over anhydrous sodium sulfate, concentrated under reduced pressure and purified by column chromatography (60% ethyl acetate/dichloromethane, NH silica gel). As a result, the compound 5 was obtained as a light yellow solid (6.8 g, 92%).

$^1$H NMR (400 MHz, CDCl$_3$) δ2.27 (t, J=2.6 Hz, 1H), 3.97 (dd, J=6.0, 2.4 Hz, 2H), 4.66 (brs, 1H), 6.53 (dd, J=4.8, 1.6 Hz, 2H), 8.26 (dd, J=4.4, 1.6 Hz, 2H); $^{13}$C NMR (100 MHz, CDCl$_3$) δ32.4, 72.0, 79.4, 108.1, 150.1, 152.3; MS (ESI) m/z 133 [M+H]$^+$ Example 2. Preparation of Compound 8 (N-propazyl, N-(pyridine-4-yl methyl)amine)

4-Pyridinecarboxyaldehyde (7, 0.5 mL, 4.7 mmol) was dissolved in dichloromethane (10 mL), to which propazyl amine (0.31 mL, 5.6 mmol) was added. Sodium triacetoxyborohydride (1.5 g, 7.05 mmol) was slowly added thereto, followed by stirring at room temperature for 2 hours. Water was added thereto and the organic compound was extracted using dichloromethane three times. The collected organic solvent was dried over anhydrous sodium sulfate, concentrated under reduced pressure and purified by column chromatography (2% methanol/dichloromethane). As a result, the compound 8 was obtained as a bright red liquid (315 mg, 46%).

$^1$H NMR (400 MHz, CDCl$_3$) δ2.28 (t, J=2.4 Hz, 1H), 3.45 (d, J=2.4 Hz, 2H), 3.93 (s, 2H), 4.24 (brs, 1H), 7.32 (dd, J=5.2, 0.8 Hz, 2H), 8.57 (dd, J=5.2, 0.8 Hz, 2H);
$^{13}$C NMR (100 MHz, CDCl$_3$) δ37.4, 50.8, 72.1, 81.3, 123.3, 148.8, 149.4; MS (ESI) m/z 147 [M+H]$^+$ A schematic reaction process of the present invention is shown in reaction formula 2 below.

[Reaction Formula 2]

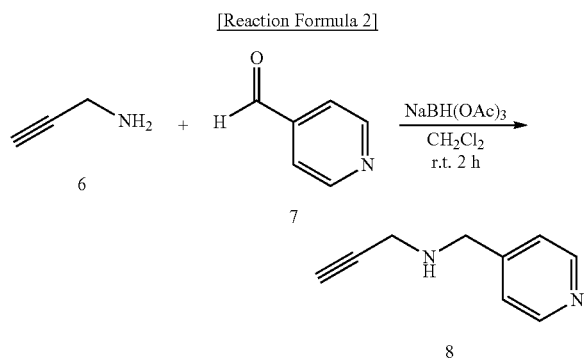

Example 3. Preparation of N-Propazyl Amine-Urea-GUL Compound

A schematic reaction process of the present invention is shown in reaction formula 3 below.

[Reaction Formula 3]

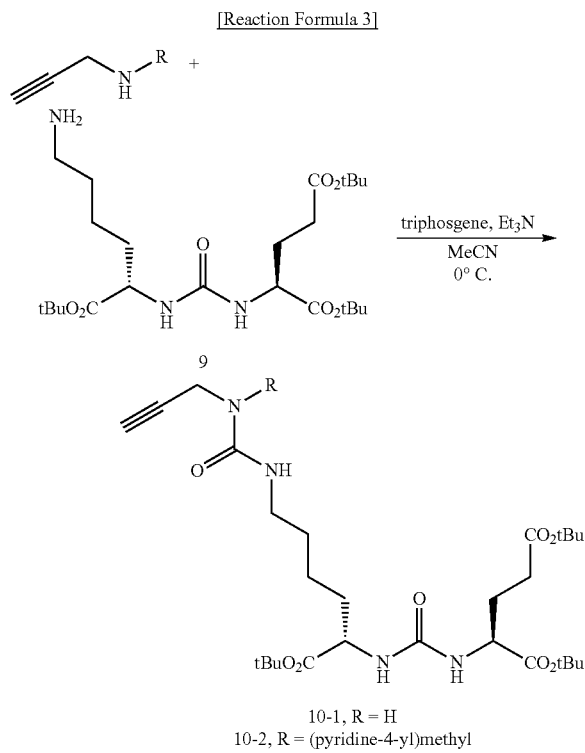

10-1, R = H
10-2, R = (pyridine-4-yl)methyl

Example 3-1. Preparation of Compound 10-1

Triphosgene (107 mg, 0.36 mmol) was dissolved in acetonitrile (5.0 mL), to which glutamate-urea-lysine (9, 500 mg, 1.03 mmol) dissolved in acetonitrile (10 mL) was slowly added at 0° C. Triethylamine (0.50 mL, 3.61 mmol) was added thereto, followed by stirring for 30 minutes. Propazyl amine (0.072 mL, 1.13 mmol) was added thereto at 0° C. 15 minutes later, the mixture was stirred at room temperature for 1 hour and then concentrated under reduced pressure. Water was added thereto and the organic compound was extracted using ethyl acetate three times. The collected organic solvent was dried over anhydrous sodium sulfate, concentrated under reduced pressure and purified by column chromatography (2% methanol/dichloromethane). As a result, the compound 10-1 was obtained as a white solid (492 mg, 84%).

$^1$H NMR (400 MHz, CDCl$_3$) δ1.25-1.30 (m, 2H), 1.44 (s, 18H), 1.48 (s, 9H), 1.51-1.60 (m, 3H), 1.67-1.76 (m, 1H), 1.80-1.90 (m, 1H), 2.05-2.13 (m, 1H), 2.18 (t, J=2.6 Hz, 1H), 2.29-2.40 (m, 2H), 3.06-3.12 (m, 1H), 3.30-3.36 (m, 1H), 3.95-4.06 (m, 2H), 4.08-4.14 (m, 1H), 4.36 (sext, J=4.4 Hz, 1H), 5.64 (d, J=7.6 Hz, 1H), 5.69 (t, J=5.2 Hz, 1H), 5.89 (t, J=5.4 Hz, 1H), 6.11 (d, J=8.4 Hz, 1H);
$^{13}$C NMR (100 MHz, CDCl$_3$) δ23.4, 27.7, 27.8, 27.9, 28.0, 29.6, 29.7, 31.7, 32.1, 39.4, 53.3, 54.2, 70.5, 80.7, 81.4, 81.5, 83.1, 158.0, 158.2, 172.0, 172.3, 174.6; MS (ESI) m/z 569 [M+H]$^+$

Example 3-2. Preparation of Compound 10-2

The compound 10-2 was obtained by the same manner as described in Example 3-1 as a light yellow solid (270 mg, 66%) except that triphosgene (64 mg, 0.211 mmol) dissolved in acetonitrile (3.0 mL), glutamate-urea-lysine (9, 300 mg, 0.62 mmol) dissolved in acetonitrile (6 mL), triethylamine (0.302 mL, 2.17 mmol) and the compound 8 (100 mg, 0.68 mmol) synthesized in Example 2 were used.

$^1$H NMR (400 MHz, CDCl$_3$) δ1.22-1.30 (m, 2H), 1.43 (s, 9H), 1.45 (s, 18H), 1.48-1.54 (m, 2H), 1.59-1.64 (m, 1H), 1.71-1.77 (m, 1H), 1.79-1.88 (m, 2H), 2.03-2.09 (m, 1H), 2.27-2.32 (m, 1H), 2.35 (t, J=2.2 Hz, 1H), 3.24 (sept, J=6.2 Hz, 2H), 4.07 (t, J=2.4 Hz, 2H), 4.27-4.35 (m, 2H), 4.60 (dd, J=20.4, 17.2 Hz, 2H), 4.92 (s, 1H), 5.24 (d, J=7.6 Hz, 1H), 5.44 (d, J=8.0 Hz, 1H), 7.24 (d, J=5.2 Hz, 2H), 8.60 (d, J=4.8 Hz, 2H);
$^{13}$C NMR (100 MHz, CDCl$_3$) δ22.3, 27.9, 28.0, 28.1, 28.4, 29.4, 31.6, 32.4, 36.8, 40.7, 49.6, 53.0, 53.3, 73.4, 78.8, 80.5, 81.7, 82.0, 122.3, 147.0, 150.2, 157.0, 157.7, 172.3, 172.4, 172.5; MS (ESI) m/z 660 [M+H]$^+$

Example 3-3. Preparation of Compound 10-3

The compound 5 (200 mg, 1.51 mmol) synthesized in Example 1-3 was dissolved in acetonitrile (5.0 mL), to which 4-nitrophenyl chloroformate (305 mg, 1.51 mmol) dissolved in acetonitrile (5.0 mL) was slowly added at 0° C. Triethyl amine (0.50 mL, 3.61 mmol) was added thereto, followed by stirring for 30 minutes. Glutamate-urea-lysine (9, 886 mg, 1.82 mmol) dissolved in acetonitrile (10 mL) was slowly added thereto at 0° C. and then diisopropylamine (0.324 mL, 1.82 mmol) was also added thereto. 15 minutes later, the mixture was stirred at 100° C. for 12 hours. After cooling the mixture to room temperature, water was added thereto and the organic compound was extracted using ethyl acetate three times. The collected organic solvent was dried over anhydrous sodium sulfate, concentrated under reduced pressure and purified by column chromatography (5% methanol/dichloromethane). As a result, the compound 10-3 was obtained as a colorless liquid (836 mg, 86%).

¹H NM (400 MHz, CDCl₃) δ1.27-1.37 (m, 2H), 1.43 (s, 9H), 1.45 (s, 18H), 1.50-1.55 (m, 2H), 1.59-1.65 (m, 1H), 1.72-1.88 (m, 2H), 2.01-2.10 (m, 1H), 2.27-2.34 (m, 1H), 2.35 (t, J=2.4 Hz, 1H), 2.16 (q, J=6.7 Hz, 2H), 4.25-4.34 (m, 2H), 4.50 (ddd, J=25.2, 18.0, 2.4 Hz, 2H), 5.21 (t, J=5.8 Hz, 1H), 5.48 (s, 1H), 5.50 (s, 1H), 7.32 (dd, J=4.8, 1.6 Hz, 2H), 8.59 (d, J=6.4 Hz, 2H);

¹³C NMR (100 MHz, CDCl₃) δ22.4, 27.9, 28.0, 28.1, 28.3, 29.4, 31.6, 32.4, 38.2, 40.7, 52.9, 53.3, 72.9, 79.3, 80.5, 81.6, 82.0, 119.5, 149.6, 151.2, 155.3, 157.1, 172.3, 172.4, 172.5; MS (ESI) m/z 646 [M+H]⁺

A schematic reaction process of the present invention is shown in reaction formula 4 below.

[Reaction Formula 4]

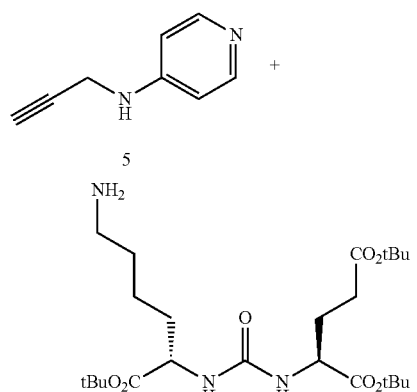

[Reaction Formula 5]

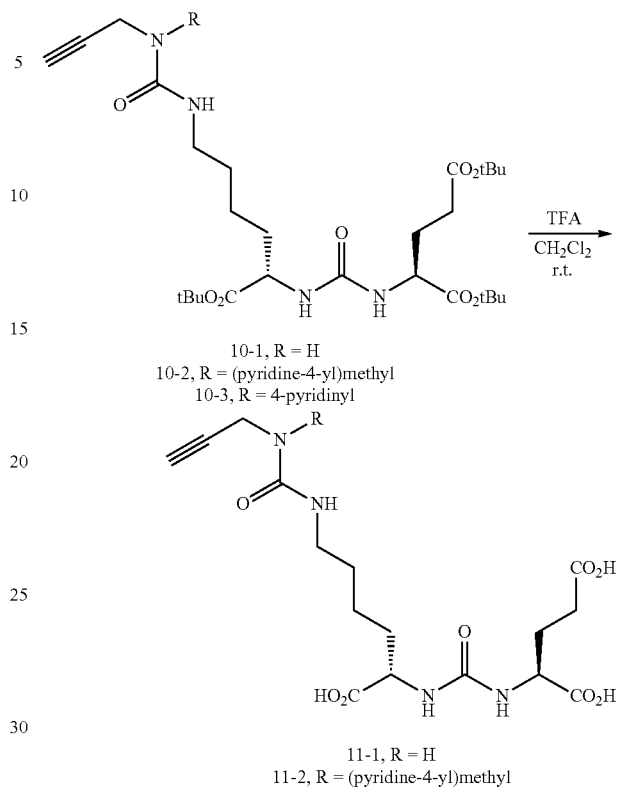

10-1, R = H
10-2, R = (pyridine-4-yl)methyl
10-3, R = 4-pyridinyl 11-1, R = H
11-2, R = (pyridine-4-yl)methyl
11-3, R = 4-pyridinyl Example 4-1. Preparation of Compound 11-1

The compound 10-1 (450 mg, 0.79 mmol) synthesized in Example 3-1 was dissolved in 60% trifluoroacetic acid/dichloromethane (2 mL), followed by stirring at room temperature for 4 hours. The reactant was concentrated under reduced pressure and purified by high performance liquid chromatography (HPLC). As a result, the compound 11-1 was obtained as a white solid (280 mg, 88%).

¹H NMR (400 MHz, DMSO-d₆) δ1.24-1.29 (m, 2H), 1.32-1.39 (m, 2H), 1.46-1.55 (m, 1H), 1.60-1.67 (m, 1H), 1.68-1.77 (m, 1H), 1.84-1.92 (m, 1H), 2.24 (td, J=7.8, 2.6 Hz, 2H), 2.96 (q, J=6.4 Hz, 2H), 3.01 (t, J=2.6 Hz, 1H), 3.77 (dd, J=5.6, 2.4, 2H), 4.05 (sext, J=7.6 Hz, 2H), 5.98 (t, J=5.6 Hz, 1H), 6.13 (t, J=5.6, 1H), 6.31 (d, J=8.4 Hz, 2H), 12.43 (brs, 3H);

¹³C NMR (100 MHz, D₂O) 521.4, 25.6, 27.8, 28.5, 29.3, 29.9, 38.7, 52.0, 52.6, 70.5, 80.4, 118.2, 158.3, 159.2, 175.6, 176.4; MS (ESI) m/z 399 [M−H]⁻

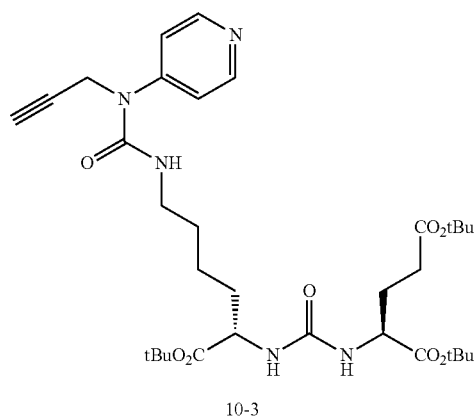

10-3

Example 4. Deprotecting Group of Compound 10

A schematic reaction process of the present invention is shown in reaction formula 5 below.

Example 4-2. Preparation of Compound 11-2

The compound 10-2 (460 mg, 0.70 mmol) synthesized in Example 3-2 was dissolved in 60% trifluoroacetic acid/dichloromethane (2 mL), followed by stirring at room temperature for 4 hours. The reactant was concentrated under reduced pressure and purified by high performance liquid chromatography (HPLC). As a result, the compound 11-2 was obtained as a white solid (289 mg, 84%).

¹H NMR (400 MHz, D₂O) δ1.10-1.18 (m, 2H), 1.29-1.36 (m, 2H), 1.44-1.52 (m, 1H), 1.56-1.63 (m, 1H), 1.71-1.80

(m, 1H), 1.91-1.99 (m, 1H), 2.28 (t, J=7.4 Hz, 2H), 2.56 (t, J=2.4 Hz, 1H), 3.03 (td, J=6.6, 2.0 Hz, 2H), 3.89 (dd, J=8.6, 5.0 Hz, 1H), 3.98 (dd, J=8.6, 5.0 Hz, 1H), 4.06 (d, J=2.4 Hz, 2H), 4.72 (s, 2H), 7.78 (d, J=5.6 Hz, 2H), 8.55 (d, J=4.8 Hz, 2H);

$^{13}$C NMR (100 MHz, D$_2$O) δ22.3, 27.3, 28.7, 30.6, 31.3, 37.7, 40.2, 50.9, 53.9, 54.3, 74.0, 78.6, 124.8, 140.9, 158.7, 158.8, 159.2, 160.3, 178.0, 178.6; MS (ESI) m/z 492 [M+H]$^+$

Example 4-3. Preparation of Compound 11-3

The compound 10-3 (650 mg, 1.01 mmol) synthesized in Example 3-3 was dissolved in 60% trifluoroacetic acid/dichloromethane (3 mL), followed by stirring at room temperature for 4 hours. The reactant was concentrated under reduced pressure and purified by high performance liquid chromatography (HPLC). As a result, the compound 11-3 was obtained as a white solid (390 mg, 81%).

$^1$H NMR (400 MHz, D$_2$O) δ1.21-1.26 (m, 2H), 1.38-1.43 (m, 2H), 1.46-1.53 (m, 1H), 1.58-1.67 (m, 1H), 1.69-1.74 (m, 1H), 1.84-1.93 (m, 1H), 2.22 (t, J=7.6 Hz, 2H), 2.61 (t, J=0.8 Hz, 1H), 3.12 (t, J=6.6 Hz, 2H), 3.92 (q, J=6.5 Hz, 2H), 4.45 (s, 2H), 7.44 (d, J=6.4 Hz, 2H), 8.27 (d, J=4.0 Hz, 2H);

$^{13}$C NMR (100 MHz, D$_2$O) δ22.4, 27.1, 27.7, 30.5, 31.2, 37.9, 40.6, 53.6, 54.1, 74.8, 76.5, 114.5, 140.7, 156.1, 156.2, 159.0, 177.7, 177.9, 178.4; MS (ESI) m/z 478 [M+H]$^+$

Example 5. Preparation of Fluorine-Triazole-Urea-GUL Compound Through Click Chemistry A schematic reaction process of the present invention is shown in reaction formula 6 below.

[Reaction Formula 6]

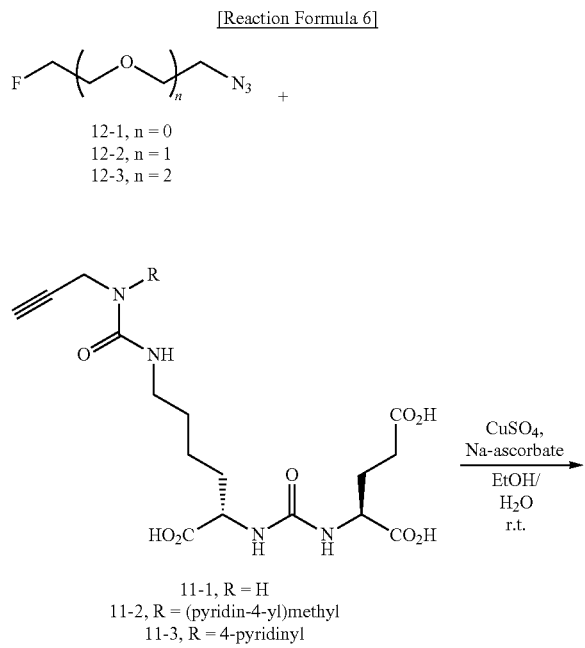

11-1, R = H
11-2, R = (pyridin-4-yl)methyl
11-3, R = 4-pyridinyl

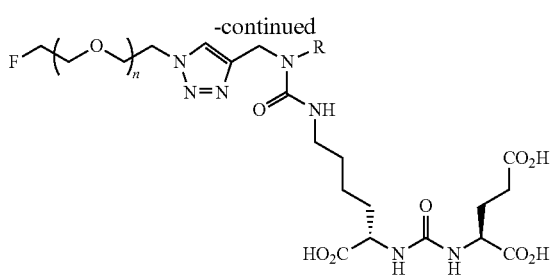

1-1, n = 0, R = H
1-2, n = 0, R = (pyridin-4-yl)methyl
1-3, n = 0, R = 4-pyridinyl
1-4, n = 1, R = H
1-5, n = 1, R = (pyridin-4-yl)methyl
1-6, n = 1, R = 4-pyridinyl
1-7, n = 2, R = H
1-8, n = 2, R = (pyridin-4-yl)methyl
1-9, n = 2, R = 4-pyridinyl Example 5-1. Preparation of Compound 1-1

2-Fluoroethyl toluenesulfonate (FCH$_2$CH$_2$OTs, 82 mg, 0.38 mmol) was dissolved in dimethylformamide (0.2 mL), to which sodium azide (73 mg, 1.13 mmol) was added, followed by stirring at 60° C. for 12 hours to synthesize fluoroethylazide (12-1). The reaction solution was filtered and washed with ethanol (0.3 mL). An aqueous solution (0.5 mL) in which the compound 11-1 (30 mg, 0.075 mmol) synthesized in Example 4-1 was dissolved was added to the filtrate. CuSO$_4$.5H$_2$O aqueous solution (0.5M, 0.046 mL, 0.023 mmol) and sodium ascorbate aqueous solution (0.5M, 0.076 mL, 0.038 mmol) were added thereto stepwise, followed by stirring at room temperature for 1 hour. The reaction mixture was filtered and washed with water. Then, the filtrate was separated by HPLC. As a result, the compound 1-1 was obtained as a white solid (7 mg, 19%).

$^1$H NMR (400 MHz, D$_2$O) δ1.17-1.28 (m, 2H), 1.30-1.37 (m, 2H), 1.50-1.59 (m, 1H), 1.64-1.72 (m, 1H), 1.77-1.87 (m, 1H), 1.98-2.05 (m, 1H), 2.36 (t, J=7.4 Hz, 2H), 2.96 (t, J=6.4 Hz, 2H), 4.03 (dd, J=8.4, 4.8 Hz, 1H), 4.11 (dd, J=8.8, 5.6 Hz, 1H), 4.24 (s, 2H), 4.56-4.57 (m, 1H), 4.65-4.68 (m, 2H), 4.75 (t, J=4.6 Hz, 1H), 7.79 (s, 1H);

$^{13}$C NMR (100 MHz, D$_2$O) δ22.0, 26.1, 28.5, 29.9, 30.4, 34.9, 39.4, 50.7 (d, J=19 Hz), 52.5, 53.1, 81.9 (d, J=168 Hz), 124.0, 146.2, 159.5, 160.2, 176.2, 177.1, 177.2; MS (ESI) m/z 488 [M−H]$^−$

Example 5-2. Preparation of Compound 1-2

2-Fluoroethyl toluenesulfonate (FCH$_2$CH$_2$OTs, 89 mg, 0.41 mmol) was dissolved in dimethylformamide (0.2 mL), to which sodium azide (79 mg, 1.22 mmol) was added, followed by stirring at 60° C. for 12 hours to synthesize fluoroethylazide (12-1). The reaction solution was filtered and washed with ethanol (0.3 mL). An aqueous solution (0.5 mL) in which the compound 11-2 (40 mg, 0.081 mmol) synthesized in Example 4-2 was dissolved was added to the filtrate. CuSO$_4$.5H$_2$O aqueous solution (0.5M, 0.049 mL, 0.024 mmol) and sodium ascorbate aqueous solution (0.5M, 0.081 mL, 0.041 mmol) were added thereto stepwise, followed by stirring at room temperature for 1 hour. The reaction mixture was filtered and washed with water. Then, the filtrate was separated by HPLC. As a result, the compound 1-2 was obtained as a white solid (33 mg, 70%).

¹H NMR (400 MHz, D₂O) δ1.21-1.34 (m, 2H), 1.41-1.50 (m, 2H), 1.59-1.68 (m, 1H), 1.71-1.80 (m, 1H), 1.86-1.96 (m, 1H), 2.08-2.16 (m, 1H), 2.45 (t, J=7.2 Hz, 2H), 3.16 (t, J=6.6 Hz, 2H), 4.09 (dd, J=8.4, 5.2 Hz, 1H), 4.21 (dd, J=8.8, 5.6 Hz, 1H), 4.63-4.70 (m, 6H), 4.84 (s, 2H), 7.72 (d, J=6.0 Hz, 2H), 7.93 (s, 1H), 8.60 (dd, J=6.8, 1.2 Hz, 2H);
¹³C NMR (100 MHz, D₂O) δ22.1, 26.0, 28.5, 29.9, 30.4, 40.0, 42.6, 50.5, 50.6 (d, J=19 Hz), 81.9 (d, J=168 Hz), 124.6, 124.7, 140.6, 143.5, 159.0, 159.2, 160.6, 176.1, 177.0, 177.1; MS (ESI) m/z 581 [M+H]⁺

Example 5-3. Preparation of Compound 1-3

2-Fluoroethyl toluenesulfonate (FCH₂CH₂OTs, 91 mg, 0.42 mmol) was dissolved in DMF (0.2 mL), to which NaN (82 mg, 1.26 mmol) was added, followed by stirring at 60° C. for 12 hours to synthesize fluoroethylazide (12-1). The reaction solution was filtered and washed with ethanol (0.3 mL). An aqueous solution (0.5 mL) in which the compound 11-3 (40 mg, 0.084 mmol) synthesized in Example 4-3 was dissolved was added to the filtrate. CuSO₄.5H₂O aqueous solution (0.5M, 0.050 mL, 0.025 mmol) and sodium ascorbate aqueous solution (0.5M, 0.084 mL, 0.042 mmol) were added thereto stepwise, followed by stirring at room temperature for 1 hour. The reaction mixture was filtered and washed with water. Then, the filtrate was separated by HPLC. As a result, the compound 1-3 was obtained as a white solid (27 mg, 57%).
¹H NMR (400 MHz, D₂O) δ1.15-1.24 (m, 2H), 1.36-1.43 (m, 2H), 1.49-1.58 (m, 1H), 1.63-1.72 (m, 1H), 1.75-1.84 (m, 1H), 1.96-2.05 (m, 1H), 2.34 (t, J=7.4 Hz, 2H), 3.15 (t, J=6.6 Hz, 2H), 4.01 (dd, J=8.8, 5.2 Hz, 1H), 4.10 (dd, J=9.0, 5.0 Hz, 1H), 4.55-4.61 (m, 3H), 4.73 (t, J=4.4 Hz, 1H), 5.05 (s, 2H), 7.47 (d, J=7.6 Hz, 2H), 7.92 (s, 1H), 8.27 (d, J=7.6 Hz, 2H);
¹³C NMR (100 MHz, D₂O) δ22.2, 26.1, 27.5, 29.9, 30.4, 40.4, 43.2, 50.7 (d, J=19 Hz), 52.4, 53.0, 81.9 (d, J=168 Hz), 114.4, 124.7, 140.7, 142.3, 156.4, 156.8, 159.2, 176.1, 176.9, 177.1; MS (ESI) m/z 567 [M+H]⁺

Example 5-4. Preparation of Compound 1-4

A solution prepared by dissolving the compound 11-1 (40 mg, 0.10 mmol) synthesized in Example 4-1 in water (0.5 mL) was added to ethanol (0.5 mL) in which 1-azido-2-(2-fluoroethoxy)ethane (12-2, 16 mg, 0.12 mmol) was dissolved. CuSO₄.5H₂O aqueous solution (0.5M, 0.060 mL, 0.030 mmol) and sodium ascorbate aqueous solution (0.5M, 0.100 mL, 0.050 mmol) were added thereto stepwise, followed by stirring at room temperature for 1 hour. The reaction mixture was filtered and washed with water. Then, the filtrate was separated by HPLC. As a result, the compound 1-4 was obtained as a white solid (20 mg, 38%).
¹H NMR (400 MHz, D₂O) δ1.14-1.22 (m, 2H), 1.24-1.32 (m, 2H), 1.45-1.54 (m, 1H), 1.59-1.66 (m, 1H), 1.72-1.82 (m, 1H), 1.93-2.02 (m, 1H), 2.31 (t, J=7.2 Hz, 2H), 2.91 (t, J=6.8 Hz, 2H), 3.51 (td, J=4.0, 0.8 Hz, 1H), 3.58 (td, J=4.0, 0.8 Hz, 1H), 3.81 (t, J=4.8 Hz, 2H), 3.98 (dd, J=8.8, 4.8 Hz, 1H), 4.06 (dd, J=9.2, 5.2 Hz, 1H), 4.20 (s, 2H), 4.28 (td, J=4.0, 0.8 Hz, 1H), 4.39 (td, J=4.0, 0.8 Hz, 1H), 4.45 (t, J=4.68 Hz, 2H), 7.78 (s, 1H);
¹³C NMR (100 MHz, D₂O) δ22.0, 26.0, 28.4, 29.9, 30.4, 34.7, 39.4, 50.3, 52.4, 53.0, 68.6, 69.7 (d, J=18 Hz), 83.1 (d, J=162 Hz), 124.3, 145.8, 159.2, 160.1, 176.1, 177.0, 177.1; MS (ESI) m/z 534 [M+H]⁺

Example 5-5. Preparation of Compound 1-5

A solution prepared by dissolving the compound 11-2 (40 mg, 0.081 mmol) synthesized in Example 4-2 in water (0.5 mL) was added to ethanol (0.5 mL) in which 1-azido-2-(2-fluoroethoxy)ethane (12-2, 13 mg, 0.097 mmol) was dissolved. CuSO₄.5H₂O aqueous solution (0.5M, 0.049 mL, 0.024 mmol) and sodium ascorbate aqueous solution (0.5M, 0.081 mL, 0.041 mmol) were added thereto stepwise, followed by stirring at room temperature for 1 hour. The reaction mixture was filtered and washed with water. Then, the filtrate was separated by HPLC. As a result, the compound 1-5 was obtained as a white solid (37 mg, 72%).
¹H NMR (400 MHz, D₂O) δ1.16-1.23 (m, 2H), 1.33-1.40 (m, 2H), 1.52-1.60 (m, 1H), 1.63-1.70 (m, 1H), 1.81-1.88 (m, 1H), 2.00-2.07 (m, 1H), 2.38 (t, J=7.4 Hz, 2H), 3.07 (t, J=6.8 Hz, 2H), 3.57 (t, J=4.0 Hz, 1H), 3.65 (t, J=4.0 Hz, 1H), 3.83 (t, J=5.0 Hz, 2H), 4.02 (dd, J=8.4, 5.2 Hz, 1H), 4.14 (dd, J=9.0, 5.0 Hz, 1H), 4.34 (t, J=4.0 Hz, 1H), 4.45-4.49 (m, 3H), 4.59 (s, 2H), 4.75 (s, 2H), 7.69 (d, J=6.8 Hz, 2H), 7.86 (s, 1H), 8.55 (d, J=6.8 Hz, 2H);
¹³C NMR (100 MHz, D₂O) δ22.2, 26.2, 28.6, 29.9, 30.5, 40.1, 42.7, 49.9, 50.6, 52.5, 53.2, 68.7, 69.7 (d, J=19 Hz), 83.2 (d, J=163 Hz), 124.7, 124.9, 140.7, 143.5, 159.1, 159.2, 160.7, 176.1, 177.0, 177.1; MS (ESI) m/z 625 [M+H]⁺

Example 5-6. Preparation of Compound 1-6

A solution prepared by dissolving the compound 11-3 (40 mg, 0.084 mmol) synthesized in Example 4-3 in water (0.5 mL) was added to ethanol (0.5 mL) in which 1-azido-2-(2-fluoroethoxy)ethane (12-2, 13 mg, 0.10 mmol) was dissolved. CuSO₄.5H₂O aqueous solution (0.5M, 0.050 mL, 0.025 mmol) and sodium ascorbate aqueous solution (0.5M, 0.084 mL, 0.042 mmol) were added thereto stepwise, followed by stirring at room temperature for 1 hour. The reaction mixture was filtered and washed with water. Then, the filtrate was separated by HPLC. As a result, the compound 1-6 was obtained as a white solid (38 mg, 75%).
¹H NMR (400 MHz, D₂O) δ1.20-1.28 (m, 2H), 1.40-1.47 (m, 2H), 1.54-1.62 (m, 1H), 1.66-1.74 (m, 1H), 1.77-1.86 (m, 1H), 1.98-2.08 (m, 1H), 2.36 (t, J=7.4 Hz, 2H), 3.17 (t, J=6.8 Hz, 2H), 3.52 (t, J=3.8 Hz, 1H), 3.60 (t, J=4.0 Hz, 1H), 3.83 (t, J=5.0 Hz, 2H), 4.05 (dd, J=8.8, 4.8 Hz, 1H), 4.12 (dd, J=9.2, 5.2 Hz, 1H), 4.28 (t, J=4.0 Hz, 1H), 4.40 (t, J=3.8 Hz, 1H), 4.48 (t, J=5.0 Hz, 2H), 5.06 (s, 2H), 7.48 (d, J=7.6 Hz, 2H), 7.90 (s, 1H), 8.28 (d, J=7.6 Hz, 2H);
¹³C NMR (100 MHz, D₂O) δ22.3, 26.2, 27.6, 29.9, 30.5, 40.5, 43.3, 50.0, 52.5, 53.1, 68.7, 69.7 (d, J=19 Hz), 83.1 (d, J=163 Hz), 114.4, 124.7, 140.7, 142.1, 156.4, 156.8, 159.2, 176.1, 176.9, 177.1; MS (ESI) m/z 611 [M+H]⁺

Example 5-7. Preparation of Compound 1-7

A solution prepared by dissolving the compound 11-1 (40 mg, 0.10 mmol) synthesized in Example 4-1 in water (0.5 mL) was added to ethanol (0.5 mL) in which 1-azido-2-(2-(2-fluoroethoxy)ethoxy)ethane (12-3, 21 mg, 0.12 mmol) was dissolved. CuSO₄.5H₂O aqueous solution (0.5M, 0.060 mL, 0.030 mmol) and sodium ascorbate aqueous solution (0.5M, 0.100 mL, 0.050 mmol) were added thereto stepwise, followed by stirring at room temperature for 1 hour. The reaction mixture was filtered and washed with water. Then, the filtrate was separated by HPLC. As a result, the compound 1-3 was obtained as a white solid (50 mg, 77%).
¹H NMR (400 MHz, D₂O) δ1.16-1.26 (m, 2H), 1.28-1.36 (m, 2H), 1.49-1.58 (m, 1H), 1.63-1.71 (m, 1H), 1.76-1.85 (m, 1H), 1.97-2.06 (m, 1H), 2.35 (t, J=7.4 Hz, 2H), 2.94 (t, J=6.4 Hz, 2H), 3.49-3.50 (m, 5H), 3.57 (td, J=4.0, 1.2 Hz, 1H), 3.81 (t, J=4.8 Hz, 2H), 4.02 (dd, J=8.8, 4.8 Hz, 1H), 4.10 (dd, J=9.0, 5.4 Hz, 1H), 4.24 (s, 2H), 4.34 (td, J=4.4, 1.2 Hz, 1H), 4.45-4.49 (m, 3H), 7.84 (s, 1H);

$^{13}$C NMR (100 MHz, D$_2$O) δ22.0, 26.1, 28.4, 29.9, 30.4, 34.6, 39.4, 50.5, 52.4, 53.0, 68.4, 69.3, 69.4, 69.7 (d, J=19 Hz), 83.1 (d, J=163 Hz), 124.5, 145.5, 159.2, 160.1, 176.2, 177.0, 177.1; MS (ESI) m/z 578 [M+H]$^+$

Example 5-8. Preparation of Compound 1-8

A solution prepared by dissolving the compound 11-2 (40 mg, 0.081 mmol) synthesized in Example 4-2 in water (0.5 mL) was added to ethanol (0.5 mL) in which 1-azido-2-(2-(2-fluoroethoxy)ethoxy)ethane (12-3, 17 mg, 0.097 mmol) was dissolved. CuSO$_4$.5H$_2$O aqueous solution (0.5M, 0.049 mL, 0.024 mmol) and sodium ascorbate aqueous solution (0.5M, 0.081 mL, 0.041 mmol) were added thereto stepwise, followed by stirring at room temperature for 1 hour. The reaction mixture was filtered and washed with water. Then, the filtrate was separated by HPLC. As a result, the compound 1-8 was obtained as a white solid (47 mg, 87%).

$^1$H NMR (400 MHz, D$_2$O) δ1.13-1.25 (m, 2H), 1.36 (quint, J=7.0 Hz, 2H), 1.50-1.60 (m, 1H), 1.63-1.72 (m, 1H), 1.79-1.88 (m, 1H), 2.00-2.09 (m, 1H), 2.38 (t, J=7.2 Hz, 2H), 3.07 (t, J=6.8 Hz, 2H), 3.52 (s, 4H), 3.54 (t, J=4.0 Hz, 1H), 3.62 (t, J=4.0 Hz, 1H), 3.80 (t, J=5.2 Hz, 2H), 4.02 (dd, J=8.6, 5.4 Hz, 1H), 4.14 (dd, J=9.0, 5.0 Hz, 1H), 4.38 (t, J=4.0 Hz, 1H), 4.46-4.51 (m, 3H), 4.58 (s, 2H), 4.75 (s, 2H), 7.70 (d, J=6.4 Hz, 2H), 7.88 (s, 1H), 8.55 (d, J=6.8 Hz, 2H);

$^{13}$C NMR (100 MHz, D$_2$O) δ22.2, 26.2, 28.6, 30.0, 30.5, 40.1, 42.7, 50.0, 50.6, 52.5, 53.2, 68.6, 69.4, 69.5, 69.7 (d, J=19 Hz), 83.3 (d, J=162 Hz), 124.7, 124.9, 140.8, 143.5, 159.1, 159.2, 160.7, 176.1, 177.0, 177.1; MS (ESI) m/z 669 [M+H]$^+$

Example 5-9. Preparation of Compound 1-9

A solution prepared by dissolving the compound 11-3 (40 mg, 0.084 mmol) synthesized in Example 4-3 in water (0.5 mL) was added to ethanol (0.5 mL) in which 1-azido-2-(2-(2-fluoroethoxy)ethoxy)ethane (12-3, 18 mg, 0.10 mmol) was dissolved. CuSO$_4$.5H$_2$O aqueous solution (0.5M, 0.050 mL, 0.025 mmol) and sodium ascorbate aqueous solution (0.5M, 0.084 mL, 0.042 mmol) were added thereto stepwise, followed by stirring at room temperature for 1 hour. The reaction mixture was filtered and washed with water. Then, the filtrate was separated by HPLC. As a result, the compound 1-9 was obtained as a white solid (30 mg, 55%).

$^1$H NMR (400 MHz, D$_2$O) δ1.15-1.22 (m, 2H), 1.35-1.40 (m, 2H), 1.47-1.56 (m, 1H), 1.61-1.68 (m, 1H), 1.72-1.81 (m, 1H), 1.93-2.03 (m, 1H), 2.31 (t, J=7.2 Hz, 2H), 3.12 (t, J=6.6 Hz, 2H), 3.43 (s, 4H), 3.46 (t, J=4.0 Hz, 1H), 3.54 (t, J=4.0 Hz, 1H), 3.75 (t, J=4.8 Hz, 2H), 3.99 (dd, J=8.8, 5.2 Hz, 1H), 4.07 (dd, J=9.2, 5.2 Hz, 1H), 4.30 (t, J=4.0 Hz, 1H), 4.41-4.44 (m, 3H), 5.00 (s, 2H), 7.43 (d, J=7.6 Hz, 2H), 7.87 (s, 1H), 8.24 (d, J=7.2 Hz, 2H);

$^{13}$C NMR (100 MHz, D$_2$O) δ22.2, 26.1, 27.5, 29.9, 30.4, 40.4, 43.2, 50.0, 52.4, 53.0, 68.6, 69.3, 69.4, 69.7 (d, J=18 Hz), 83.1 (d, J=162 Hz), 114.3, 124.6, 140.6, 142.0, 156.3, 156.8, 159.2, 176.1, 176.9, 177.1; MS (ESI) m/z 655 [M+H]$^+$

Example 6. Synthesis of $^{125}$I-MIP1095 Compound

A schematic reaction process of the present invention is shown in reaction formula 7 below.

[Reaction Formula 7]

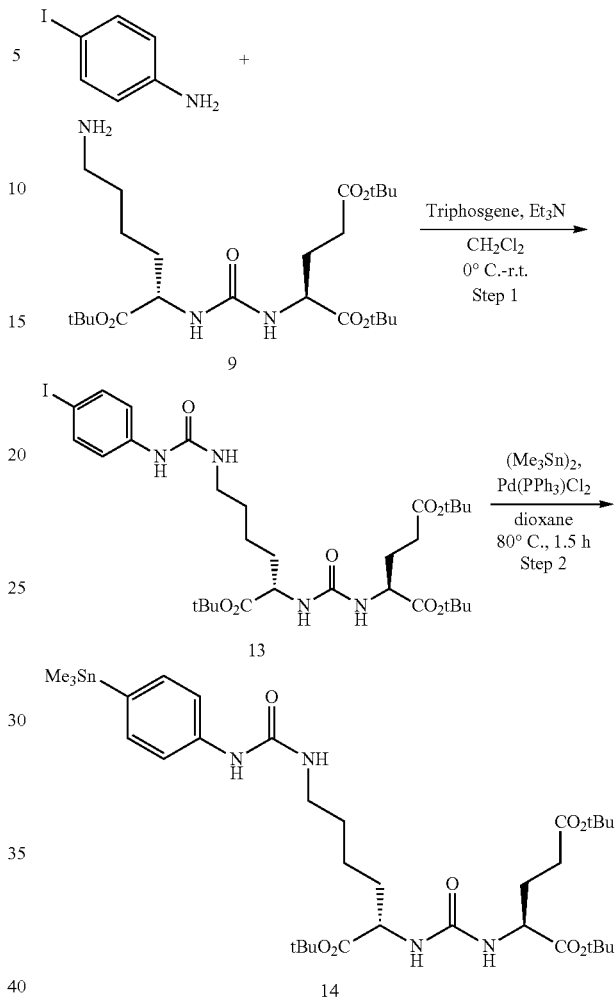

Example 6-1. Preparation of Compound 13 (Step 1)

Triphosgene (21 mg, 0.071 mmol) was dissolved in dichloromethane (5 mL), to which 4-iodoaniline (45 mg, 0.205 mmol) dissolved in dichloromethane (5 mL) was slowly added at 0° C. Triethylamine (0.57 mL, 0.410 mmol) was added thereto, followed by stirring for 30 minutes. Glutamate-urea-lysine (9, 100 mg, 0.205 mmol) dissolved in dichloromethane (10 mL) was slowly added thereto at 0° C. Triethylamine (0.57 mL, 0.410 mmol) was also added thereto. 15 minutes later, the mixture was stirred at room temperature for 5 hours. The mixture was concentrated under reduced pressure and purified by column chromatography (2% methanol/dichloromethane). As a result, the compound 13 was obtained as a white liquid (66 mg, 44%).

$^1$H NMR (400 MHz, CDCl$_3$) δ1.20-1.27 (m, 2H), 1.37 (s, 9H), 1.40 (s, 9H), 1.44 (s, 9H), 1.47-1.57 (m, 2H), 1.71-1.81 (m, 2H), 1.83-1.91 (m, 1H), 2.03-2.11 (m, 1H), 2.37 (sext, J=8.2 Hz, 2H), 3.01-3.07 (m, 1H), 3.51-3.56 (m, 1H), 3.97-4.01 (m, 1H), 4.26-4.32 (m, 1H), 5.75 (d, J=7.2 Hz, 1H), 6.31 (q, J=3.4 Hz, 1H), 6.40 (d, J=8.0 Hz, 1H), 7.27 (d, J=8.8 Hz, 2H), 7.52 (d, J=8.8 Hz, 2H), 7.90 (s, 1H);

$^{13}$C NMR (100 MHz, CDCl$_3$) δ24.5, 27.1, 27.8, 27.9, 28.0, 29.6, 31.7, 32.0, 39.1, 53.8, 54.9, 81.0, 81.8, 83.6, 83.7, 120.2, 137.5, 140.2, 155.6, 158.5, 171.8, 172.0, 175.3; MS (ESI) m/z 733 [M+H]$^+$

Example 6-2. Preparation of Compound 14 (Step 2)

The compound 13 (50 mg, 0.068 mmol) synthesized in step 1 above was dissolved in 1,4-dioxane (1.0 mL), to which hexamethylditin (0.043 mL, 0.206 mmol) and bis (triphenylphosphine)palladium(II) dichloride (4.8 mg, 0.005 mmol) were added stepwise, followed by stirring at 110° C. for 1.5 hours. After cooling the mixture to room temperature, potassium fluoride aqueous solution (50 mL) was added thereto and the organic compound was extracted using ethyl acetate three times. The collected organic solvent was dried over anhydrous sodium sulfate, concentrated under reduced pressure and purified by column chromatography (triethylamine:ethyl acetate:n-hexane, 1:40:59). As a result, the compound 14 was obtained as a white solid (28 mg, 53%).

$^1$H NMR (400 MHz, CDCl$_3$) δ0.25 (s, 9H), 1.22-1.29 (m, 2H), 1.38 (s, 9H), 1.41 (s, 9H), 1.43 (s, 9H), 1.48-1.59 (m, 2H), 1.72-1.78 (m, 1H), 1.81-1.91 (m, 1H), 2.05-2.13 (m, 2H), 2.34-2.43 (m, 2H), 3.04-3.09 (m, 1H), 3.51-3.55 (m, 1H), 4.04 (pent, J=4.9 Hz, 1H), 4.33 (sext, J=4.5 Hz, 1H), 5.73 (d, J=6.8 Hz 1H), 6.23 (br s, 1H), 6.32 (d, J=8.4 Hz, 1H), 7.35 (d, J=8.0 Hz, 2H), 7.43 (d, J=8.4 Hz, 2H), 7.73 (s, 1H);

$^{13}$C NMR (100 MHz, CDCl$_3$) δ−9.5, 24.2, 27.4, 27.8, 27.9, 28.0, 29.7, 31.8, 32.1, 39.1, 53.7, 54.7, 80.9, 81.7, 83.5, 118.4, 133.6, 136.2, 140.4, 155.9, 158.3, 171.9, 172.2, 175.1; MS (ESI) m/z 771 [M+2H]+

Example 7. Preparation of $^{18}$F-Labelled Compound ([$^{18}$F]1)

A schematic reaction process of the present invention is shown in reaction formula 8 below.

[Reaction Formula 8]

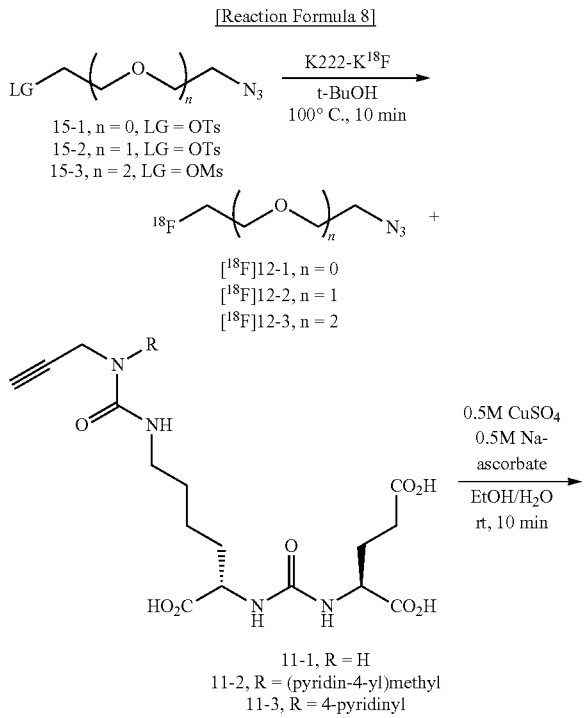

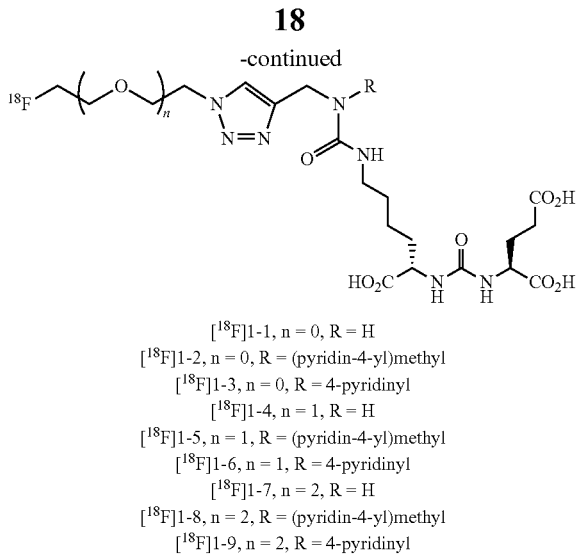

[$^{18}$F]1-1, n = 0, R = H
[$^{18}$F]1-2, n = 0, R = (pyridin-4-yl)methyl
[$^{18}$F]1-3, n = 0, R = 4-pyridinyl
[$^{18}$F]1-4, n = 1, R = H
[$^{18}$F]1-5, n = 1, R = (pyridin-4-yl)methyl
[$^{18}$F]1-6, n = 1, R = 4-pyridinyl
[$^{18}$F]1-7, n = 2, R = H
[$^{18}$F]1-8, n = 2, R = (pyridin-4-yl)methyl
[$^{18}$F]1-9, n = 2, R = 4-pyridinyl Example 7-1. Preparation of [$^{18}$F]1-1 Compound Distilled water (3 mL) was poured down on Chromafix® (HCO$_3$), which passed through [$^{18}$F] fluoride aqueous solution (508 mCi), and then ethanol (1 mL) was poured down thereto. Krytofix222-Potassium methanesulfonate (10 mg) was dissolved in ethanol (1 mL), through which Chromafix® was passed, and the solvent was removed by blowing nitrogen to the solution at 100° C. 2-Azidoethyl 4-toluenesulfonate 15-1 (1.2 mg) was dissolved in t-butanol (500 μL), which was placed in a reaction vessel containing [$^{18}$F] fluoride, followed by reaction at 100° C. for 10 minutes (preparation of [$^{18}$F]12-1). The reaction mixture was cooled to room temperature. Then, 150 μL (137 mCi) of the reaction mixture was placed in another reaction vessel, to which ethanol (150 μL), an aqueous solution containing the compound 11-1 (1 mg) dissolved therein (100 μL), 0.5M CuSO$_4$ (5 μL) and 0.5M sodium ascorbate (10 μL) were added in that order, followed by reaction at room temperature for 10 minutes. Distilled water (2 mL) was added to the reaction mixture, which was filtered and separated by HPLC. As a result, the compound [$^{18}$F]1-1 (55.3 mCi) was obtained.

HPLC condition: Column, XTerra MS C18 (250 mm×10 mm); Moving phase, 5-30% acetonitrile/water (0.1% TFA), 70 minutes; Flow rate, 4 mL/min.; UV, 230 mm; Retention time, 15-20 minutes.

Example 7-2. Preparation of [$^{18}$F]1-2 Compound

150 μL (122 mCi) of t-butanol containing [$^{18}$F]12-1 prepared in Example 7-1 dissolved therein was placed in another reaction vessel, to which ethanol (150 μL), an aqueous solution containing the compound 11-2 (1.5 mg) dissolved therein (100 μL), 0.5M CuSO$_4$ (5 μL) and 0.5M sodium ascorbate (10 μL) were added in that order, followed by reaction at room temperature for 10 minutes. Distilled water (2 mL) was added to the reaction mixture, which was filtered and separated by HPLC. As a result, the compound [$^{18}$F]1-2 (39 mCi) was obtained.

HPLC condition: Column, XTerra MS C18 (250 mm×10 mm); Moving phase, 5-30% acetonitrile/water (0.1% TFA) 50 minutes; Flow rate, 4 mL/min.; UV, 230 mm; Retention time, 17-20 minutes.

Example 7-3. Preparation of [$^{18}$F]1-3 Compound

200 μL (120 mCi) of t-butanol containing [$^{18}$F]12-1 prepared in Example 7-1 dissolved therein was placed in another reaction vessel, to which ethanol (150 μL), an aqueous solution containing the compound 11-3 (1.5 mg) dissolved therein (100 μL), 0.5M CuSO$_4$ (5 μL) and 0.5M sodium ascorbate (10 μL) were added in that order, followed by reaction at room temperature for 10 minutes. Distilled water (2 mL) was added to the reaction mixture, which was filtered and separated by HPLC. As a result, the compound [$^{18}$F]1-3 (19.9 mCi) was obtained.

HPLC condition: Column, XTerra MS C18 (250 mm×10 mm); Moving phase, 5-30% acetonitrile/water (0.1% TFA), 90 minutes; Flow rate, 4 mL/min.; UV, 230 mm; Retention time, 14-16 minutes.

Example 7-4. Preparation of [$^{18}$F]1-4 Compound

Distilled water (3 mL) was poured down on Chromafix® (HCO$_3$), which passed through [$^{18}$F] fluoride aqueous solution (493 mCi), and then ethanol (1 mL) was poured down thereto. Krytofix222-Potassium methanesulfonate (10 mg) was dissolved in ethanol (1 mL), through which Chromafix® was passed, and the solvent was removed by blowing nitrogen to the solution at 100° C. 2-(2-Azidoethoxy)ethyl methanesulfonate 15-2 (2.2 mg) was dissolved in t-butanol (500 μL), which was placed in a reaction vessel containing [$^{18}$F]fluoride, followed by reaction at 10° C. for 10 minutes (preparation of [$^{18}$F]12-2). The reaction mixture was cooled to room temperature. Then, 150 μL (81.3 mCi) of the reaction mixture was placed in another reaction vessel, to which ethanol (150 μL), an aqueous solution containing the compound 11-1 (2 mg) dissolved therein (100 μL), 0.5M CuSO$_4$ (5 μL) and 0.5M sodium ascorbate (10 μL) were added in that order, followed by reaction at room temperature for 10 minutes. Distilled water (2 mL) was added to the reaction mixture, which was filtered and separated by HPLC. As a result, the compound [$^{18}$F]1-4 (16.8 mCi) was obtained.

HPLC condition: Column, XTerra MS C18 (250 mm×10 mm); Moving phase, 5-30% acetonitrile/water (0.1% TFA), 70 minutes; Flow rate, 4 mL/min.; UV, 254 mm; Retention time, 26-29 minutes.

Example 7-5. Preparation of [$^{18}$F]1-5 Compound

150 μL (88.4 mCi) of t-butanol containing [$^{18}$F]12-2 prepared in Example 7-4 dissolved therein was placed in another reaction vessel, to which the compound 11-2 (1.5 mg) dissolved in distilled water (100 μL), 0.5M CuSO$_4$ (5 μL) and 0.5M sodium ascorbate (10 μL) were added in that order, followed by reaction at room temperature for 10 minutes. Distilled water (2 mL) was added to the reaction mixture, which was filtered and separated by HPLC. As a result, the compound [$^{18}$F]1-5 (26.5 mCi) was obtained.

HPLC condition: Column, XTerra MS C18 (250 mm×10 mm); Moving phase, 5-30% acetonitrile/water (0.1% TFA), 50 minutes; Flow rate, 4 mL/min.; UV, 254 mm; Retention time, 29 minutes.

Example 7-6. Preparation of [$^{18}$F]1-6 Compound

100 μL (88.0 mCi) of t-butanol containing [$^{18}$F]12-2 prepared in Example 7-4 dissolved therein was placed in another reaction vessel, to which the compound 11-3 (2 mg) dissolved in distilled water (100 μL), 0.5M CuSO$_4$ (5 μL) and 0.5M sodium ascorbate (10 μL) were added in that order, followed by reaction at room temperature for 10 minutes. Distilled water (2 mL) was added to the reaction mixture, which was filtered and separated by HPLC. As a result, the compound [$^{18}$F]1-6 (16.1 mCi) was obtained.

Figure 1B:
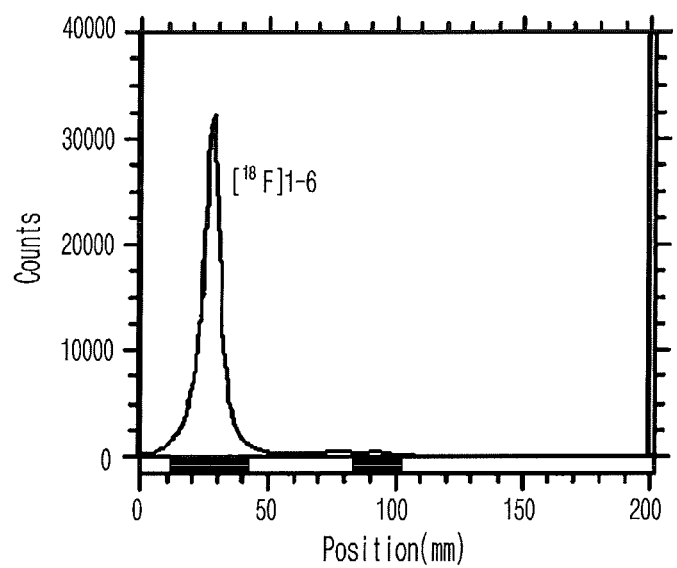
Figure 2:
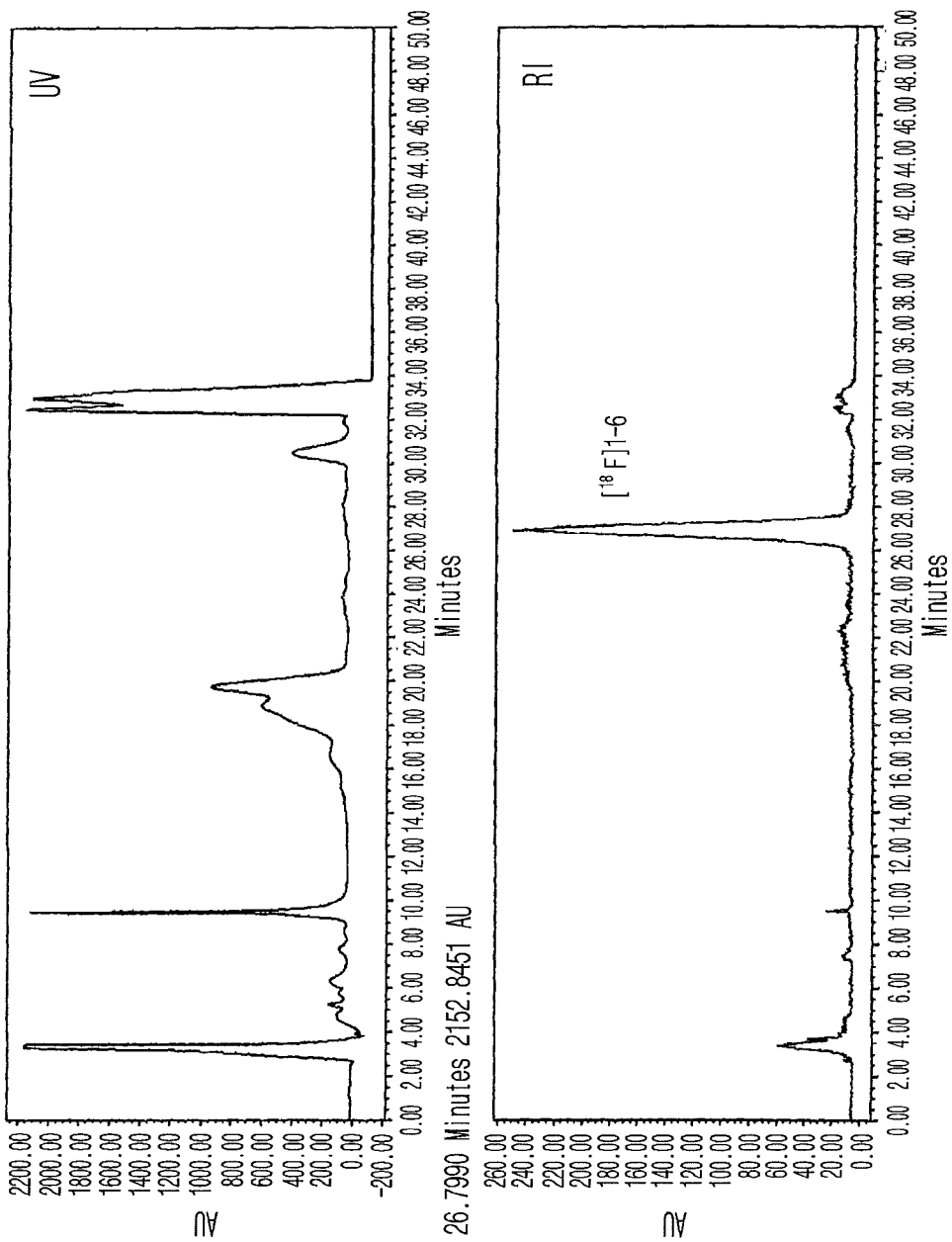
FIG. 2 is a diagram illustrating the results of HPLC separation according to the preparation step of the compound [$^{18}$F] 1-6.

FIGS. 1A, 1B and 2 are graphs illustrating the results of Radio-TLC and HPLC separation according to the preparation step of the compound [$^{18}$F]1-6.

HPLC condition: Column, XTerra MS C18 (250 mm×10 mm); Moving phase, 5-30% acetonitrile/water (0.1% TFA), 50 minutes; Flow rate, 4 mL/min.; UV, 254 mm; Retention time, 27 minutes.

Example 7-7. Preparation of [$^{18}$F]1-7 Compound

Distilled water (3 mL) was poured down on Chromafix® (HCO$_3^-$), which passed through [$^{18}$F] fluoride aqueous solution (574 mCi), and then ethanol (1 mL) was poured down thereto. Krytofix222-Potassium methanesulfonate (10 mg) was dissolved in ethanol (1 mL), through which Chromafix® was passed, and the solvent was removed by blowing nitrogen to the solution at 100° C. 2-(2-(2-Azidoethoxy)ethoxy)ethyl methanesulfonate 15-3 (2.7 mg) was dissolved in t-butanol (500 μL), which was placed in a reaction vessel containing [$^{18}$F]fluoride, followed by reaction at 100° C. for 10 minutes (preparation of [$^{18}$F]12-3). Upon completion of the reaction, the solvent was removed by gently blowing nitrogen gas to the solution at 100° C., and then the reaction mixture was dissolved in ethanol (300 μL). 100 μL (87 mCi) of the ethanol solution containing [$^{18}$F]12-3 dissolved therein was placed in another reaction vessel, to which distilled water containing the compound 11-1 (2 mg) dissolved therein (100 μL), 0.5M CuSO$_4$ (5 μL) and 0.5M sodium ascorbate (10 μL) were added in that order, followed by reaction at room temperature for 10 minutes. Distilled water (2 mL) was added to the reaction mixture, which was filtered and separated by HPLC. As a result, the compound [$^{18}$F]1-7 (31.2 mCi) was obtained.

HPLC condition: Column, XTerra MS C18 (250 mm×10 mm); Moving phase, 5-30% acetonitrile/water (0.1% TFA), 50 minutes; Flow rate, 4 mL/min.; UV, 254 mm; Retention time, 29 minutes.

Example 7-8. Preparation of [$^{18}$F]1-8 Compound

100 μL (87 mCi) of the ethanol solution (100 μL) containing [$^{18}$F]12-3 prepared in Example 7-7 dissolved therein was placed in another reaction vessel, to which the compound 11-2 (1.5 mg) dissolved in distilled water (100 μL), 0.5M CuSO$_4$ (5 μL) and 0.5M sodium ascorbate (10 μL) were added in that order, followed by reaction at room temperature for 10 minutes. Distilled water (2 mL) was added to the reaction mixture, which was filtered and separated by HPLC. As a result, the compound [$^{18}$F]1-8 (26.5 mCi) was obtained.

HPLC condition: Column, XTerra MS C18 (250 mm×10 mm); Moving phase, 5-30% acetonitrile/water (0.1% TFA), 50 minutes; Flow rate, 4 mL/min.; UV, 254 mm; Retention time, 27 minutes.

Example 7-9. Preparation of [$^{18}$F]1-9 Compound

100 μL (89 mCi) of the ethanol solution (100 μL) containing [$^{18}$F]12-3 prepared in Example 7-7 dissolved therein was placed in another reaction vessel, to which the compound 11-3 (2 mg) dissolved in distilled water (100 μL), 0.5M CuSO$_4$ (5 μL) and 0.5M sodium ascorbate (10 μL)

were added in that order, followed by reaction at room temperature for 10 minutes. Distilled water (2 mL) was added to the reaction mixture, which was filtered and separated by HPLC. As a result, the compound [$^{18}$F] 1-9 (18.9 mCi) was obtained.

HPLC condition: Column, XTerra MS C18 (250 mm×10 mm); Moving phase, 5-30% acetonitrile/water (0.1% TFA), 50 minutes; Flow rate, 4 mL/min.; UV, 254 mm; Retention time, 27.5 minutes.

Comparative Example 1. Preparation of [$^{125}$I]15 ([$^{121}$I]MIP-1095) Compound The compound 14 (0.1 mg) synthesized in Example 6-2 was dissolved in ethanol (250 μL), which was added to sodium [$^{125}$I]iodide aqueous solution (4.6 mCi, 50 μL), followed by stirring. 1N HCl aqueous solution (100 μL) and 3% $H_2O_2$ were added thereto, followed by stirring at room temperature for 10 minutes. 0.1M sodium thiosulfate aqueous solution (200 μL) and distilled water (18 mL) were added to the reaction mixture, which was passed through C-18 Sep-Pak, followed by pouring with distilled water (20 mL). Acetonitrile (2.0 mL) was poured into C-18 Sep-Pak, and then the acetonitrile was removed by blowing nitrogen to the solution. Dichloromethane (0.2 mL) and trifluoroacetic acid (0.8 mL) were added thereto, followed by stirring at room temperature for 20 minutes. The reaction solvent was removed by blowing nitrogen to the solution. Distilled water (2 mL) was added to the reaction mixture, which was separated by HPLC. As a result, the compound [$^{125}$I]15 (1.1 mCi, 24%) was obtained.

HPLC condition: Column, XTerra MS C18 (250 mm×10 mm); Moving phase, 30% acetonitrile/water (0.1% TFA); Flow rate, 5 mL/min; UV, 254 mm; Retention time, 10.4 minutes.

A schematic reaction process of the present invention is shown in reaction formula 9 below.

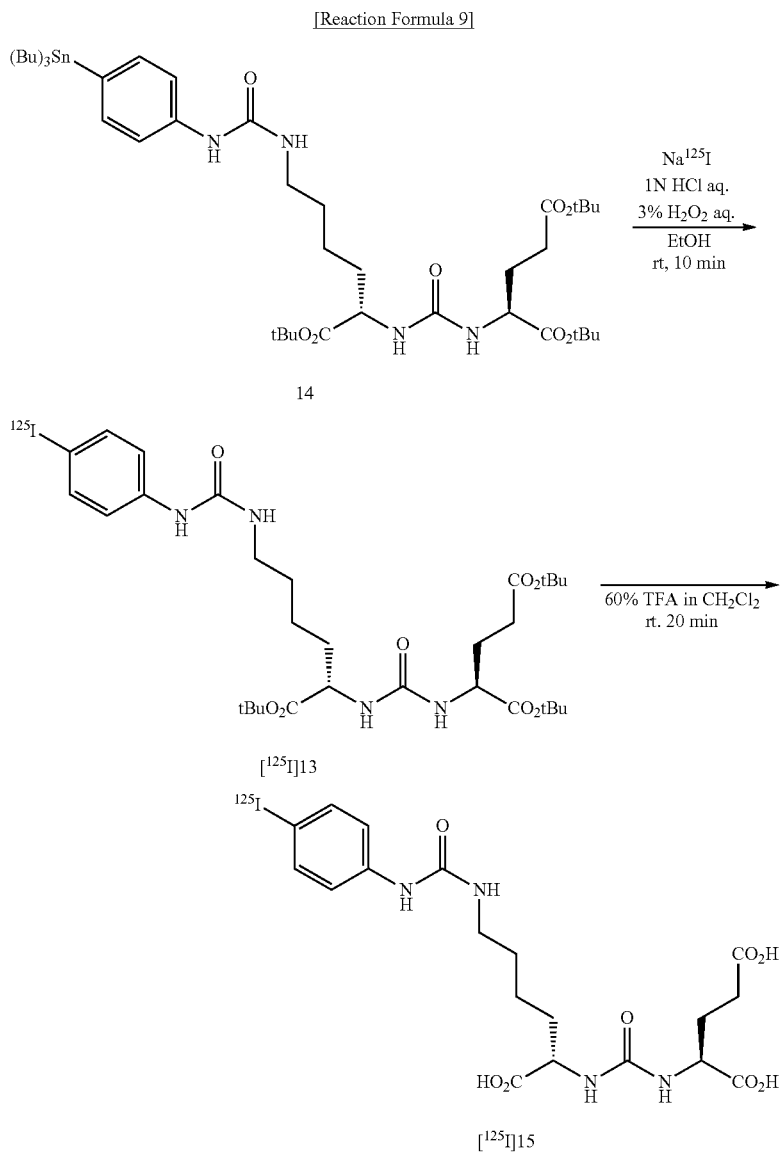

[Reaction Formula 9]

Reference Example 1. Material Preparation

A human prostate cancer cell line (22RV1) used herein was purchased from American Type Culture Collection (ATCC). PC3 PIP (PSMA$^+$) and PC3 flu (PSMA$^-$), the human prostate cancer cell lines, were provided by Dr. Martin G. Pomper (Johns Hopkins Medical School, Baltimore, Md.). The human prostate cancer cell lines were maintained in RPMI1640 medium supplemented with 10% fetal bovine serum (FBS) and 1% antibiotic/antifungal agent. In the culture of PC3 PIP (PSMA+) and PC3 flu (PSMA−) cell lines, puromycin was additionally added at the concentration of 2 μg/mL.

As test animals, 6 weeks old male nude mice (Narabio, Seoul, Korea) were used.

Experimental Example 1. Measurement of Binding Capacity

To confirm the binding capacity of the $^{18}$F-labelled compound obtained in Example 7 and the [$^{125}$I]15 obtained in Comparative Example 1 of the present invention to prostate cancer cell line, the following experiment was performed.

RPMI1640 supplemented with 1% BSA (bovine serum albumin) was used as a buffer solution.

[$^{125}$I]15 (0.1 nM) was added to a vessel containing 22RV1 cells (5×10$^4$), to which [$^{18}$F]1-1 to [$^{18}$F]1-9 compounds were loaded at 9 concentrations (1.00λ10$^{-4}$ to 1.00λ10$^{-12}$M), followed by stirring at 37° C. for 2 hours. Upon completion of the stirring, the vessel was washed with 2 mL of PBS solution three times, and then the remaining radioactivity and 50% inhibition concentration (nonlinear regression method) were measured using a gamma counter (2480 WIZARD2 Gamma Counter PerkinElmer Co., MA) and GraphPad Prism (GraphPad Software, Inc., CA).

Table 1 is a table showing the measurement results.

As a result, as shown in Table 1, the IC$_{50}$ value of [$^{18}$F]1-6 (Example 7-6) in which pyridine was directly bound to the urea functional group was the best (5.08), the IC$_{50}$ value of [$^{18}$F]1-3 (Example 7-3) without pyridine was worse more than 70 times, and the IC$_{50}$ value of [$^{18}$F]1-9 (Example 7-9) in which methylpyridine was bound was worse more than 40 times. Therefore, it was confirmed that the pyridine of ([$^{18}$F]1-6 (Example 7-6) formed a high lipophilic bond with the PSMA protein.

Example 7-4 to Example 7-6 were compared. As a result, it was confirmed that the longer the distance between the triazole group and the $^{18}$F isotope, the better the IC$_{50}$ value.

Therefore, it was found that the [$^1$F]1-6 (Example 7-6) having pyridine directly bound to urea and having a triethylene glycol group between the $^{18}$F isotope and the triazole group was most strongly bound to the PSMA protein.

The IC$_{50}$ value of [$^{18}$F]DCFPyL (Comparative Example 1) was 30.71. Therefore, [$^{18}$F]1-6 (Example 7-6) of the present invention was confirmed to have about 6 times higher binding capacity.

TABLE 1

| Compound | IC$_{50}$ (Mean ± SD, nM) |
| --- | --- |
| Comparative Example 1 | 30.71 ± 10.18 |
| Example 7-1 | 635.13 ± 262.66 |
| Example 7-2 | 65.34 ± 39.08 |
| Example 7-3 | 391.00 ± 227.94 |
| Example 7-4 | 56.99 ± 33.02 |
| Example 7-5 | 11.80 |
| Example 7-6 | 5.08 ± 2.57 |
| Example 7-7 | 64.62 ± 38.44 |

TABLE 1-continued

| Compound | IC$_{50}$ (Mean ± SD, nM) |
| --- | --- |
| Example 7-8 | 284.10 ± 115.70 |
| Example 7-9 | 235.63 ± 190.70 |

Experimental Example 2. Measurement of Cellular Internalization

To confirm the cellular internalization characteristics of the $^{18}$F-labelled compound obtained in Example 7 and the [$^{125}$I]15 obtained in Comparative Example 1 of the present invention to prostate cancer cell line, the following experiment was performed.

3.7 MBq (100 μCi) of Example 7-3, Example 7-6, and Comparative Example 1 were added to PC-3 PIP (1×10$^6$/1 mL), which was washed twice each with 2 mL of PBS solution after 30, 60, and 120 minutes. Then, the membrane protein and the cytoplasmic protein were separated by using Mem-PER Plus Membrane Protein Extraction Kit and NE-PER Nuclear and Cytoplasmic Extraction Kit (ThermoFisher Scientific). The internalization rate (%) was confirmed by obtaining the radioactivity ratio in the cytoplasmic protein to the total radioactivity.

Table 2 shows the rate of cellular internalization.

As a result, as shown in Table 2, it was confirmed that the three compounds were well internalized in prostate cancer cells without any significant difference and the internalization was almost complete within the first 30 minutes without any change over the time.

TABLE 2

| Classify | Time (min) | % Internalization ratio (Mean ± SD) |
| --- | --- | --- |
| Example 7-3 | 30 | 94.24 ± 0.80 |
|  | 60 | 92.33 ± 1.89 |
|  | 120 | 85.77 ± 6.12 |
|  | 240 | 95.47 ± 1.52 |
| Example 7-6 | 30 | 93.30 ± 2.11 |
|  | 60 | 91.89 ± 5.76 |
|  | 120 | 94.77 ± 2.92 |
|  | 240 | 96.32 ± 1.08 |
| Comparative Example 1 | 30 | 91.27 ± 4.03 |
|  | 60 | 86.91 ± 8.13 |
|  | 120 | 94.31 ± 2.94 |
|  | 240 | 95.01 ± 2.58 |

Experimental Example 3. Measurement of MicroPET/CT in Mice Transplanted with Prostate Cancer Cell Lines To confirm the binding properties of the $^{18}$F-labelled compound obtained in Example 7 and the [$^{125}$I]15 obtained in Comparative Example 1 of the present invention to prostate-specific cell membrane antibody, the following experiment was performed.

A tumor model was prepared by subcutaneously injecting PSMA+ PC-3 PIP cells (a human prostate cancer cell line) to the right side of the nude mouse hind leg and subcutaneously injecting PSMA PC-3 flu cells to the left side of the nude mouse hind leg as the control. In addition, each of Example 7-3 and Example 7-6 was intravenously injected with 5.5 to 7.4 MBq (200 μL), and PET/CT images were obtained using small animal nanoScan PET/CT (Mediso, Budapest, Hungary) for 60 minutes. The obtained PET/CT image results were quantitatively analyzed using InterView™ FUSION software (Mediso). Comparative Example 1 was used as the control compound.

Figure 3:
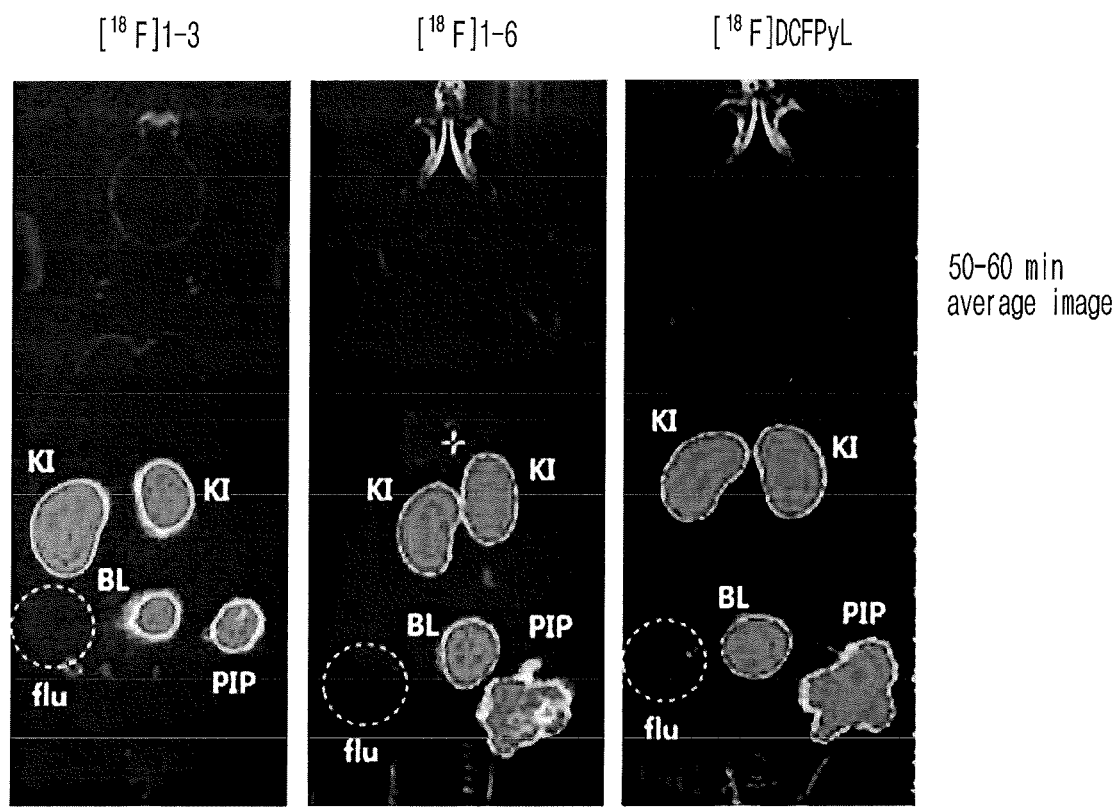
FIG. 3 is a diagram illustrating the results of MicroPET/CT of the prostate cancer mouse.
Figure 4A:
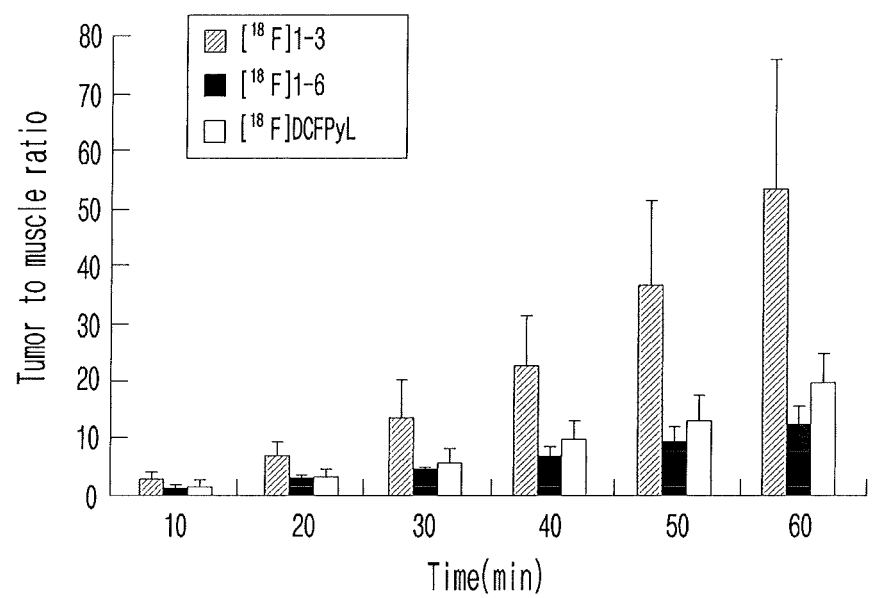
FIGS. 4A, 4B and 4C are graphs illustrating the intake ratio of muscle, liver and spleen compared to tumor.
Figure 4B:
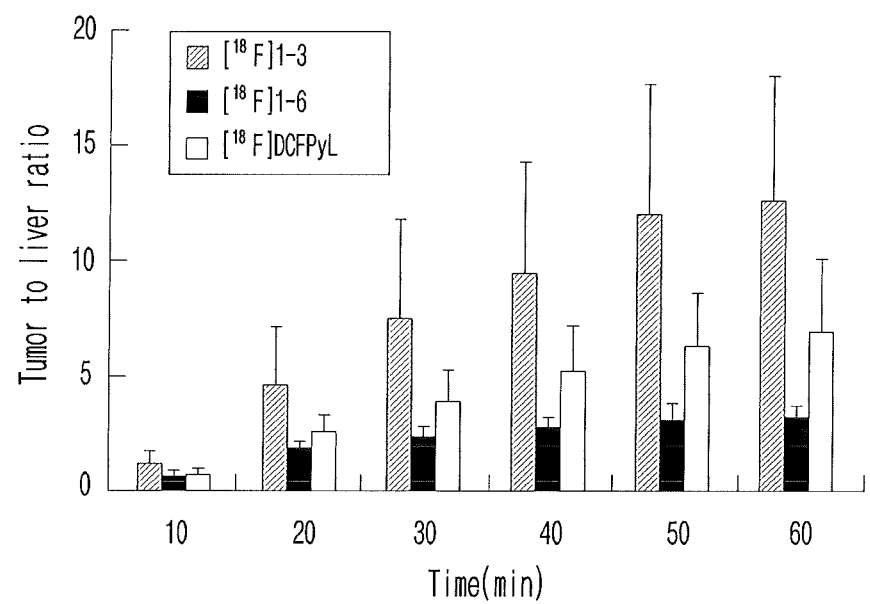
Figure 4C:
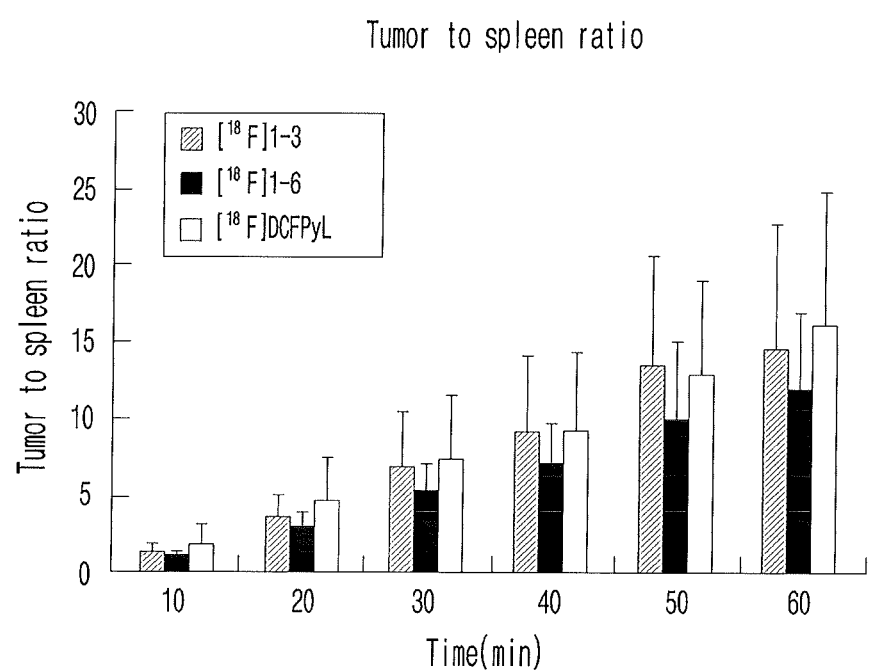

FIG. 3 is a diagram illustrating the results of MicroPET/CT of the prostate cancer mouse. FIGS. 4A to 4C are graphs illustrating the intake ratio of muscle, liver and spleen compared to tumor.

As shown in FIG. 3, it was confirmed that Example 7-3, Example 7-6, and Comparative Example 1 were rapidly excreted through the kidneys and bladder, and they selectively bound to PSMA+PC-3 PIP tumors. As shown in FIGS. 4A to 4C, it was confirmed that Example 7-3 showed relatively higher tumor/muscle (tumor to muscle ratio) and tumor/liver (tumor to liver ratio) intake ratios than those of Example 7-6 and Comparative Example 1.

Experimental Example 4. Biodistribution Test with Prostate Cancer Model Mouse

To confirm the biodistribution of the $^{18}$F-labelled compound obtained in Example 7 and the [$^{125}$I]15 obtained in Comparative Example 1 of the present invention in the prostate cancer model mouse, the following experiment was performed.

A tumor model was prepared by subcutaneously injecting PSMA+ PC-3 PIP cells (a human prostate cancer cell line) to the right side of the nude mouse (6 weeks old, 20-25 g) hind leg and subcutaneously injecting PSMA− PC-3 flu cells to the left side of the nude mouse hind leg as the control. The compounds of Example 7-3 and Example 7-6 were synthesized, which were injected into the tail vein of the mouse at the dose of 3.7 MBq (100 μCi), respectively. Each organ (blood, muscle, fat, heart, lung, liver, spleen, stomach, intestine, kidney, bone and tumor) was extracted at 30 minutes, 1 hour, 2 hours and 4 hours later and the radioactivity thereof was measured using a gamma counter.

Figure 5A:
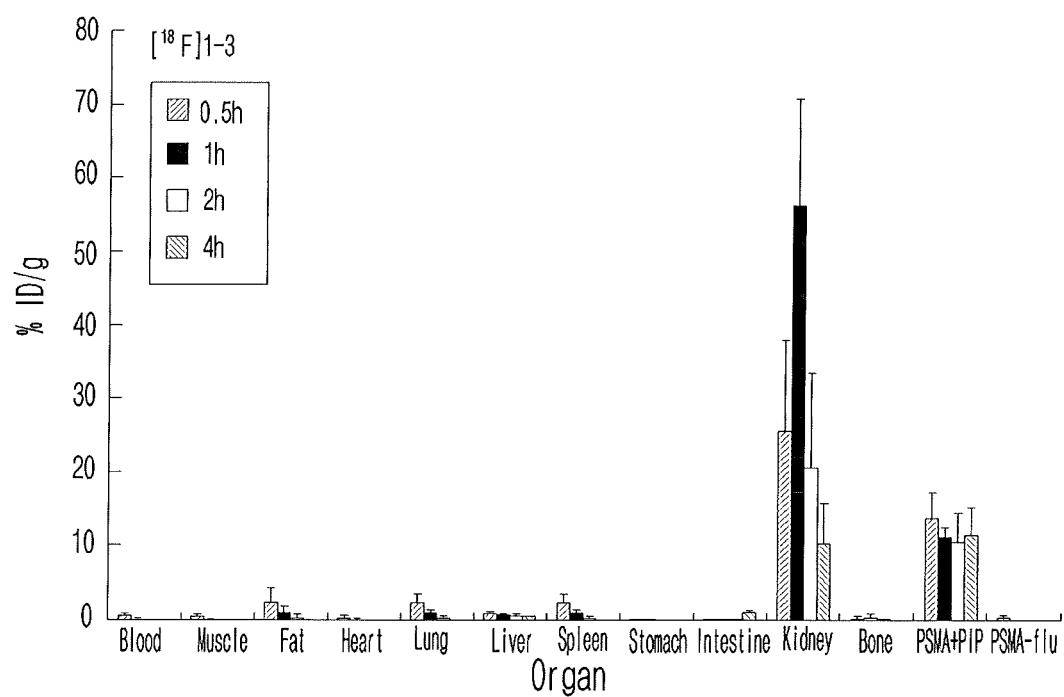
FIGS. 5A and 5B are graphs illustrating the organ biodistribution over the time.
Figure 5B:
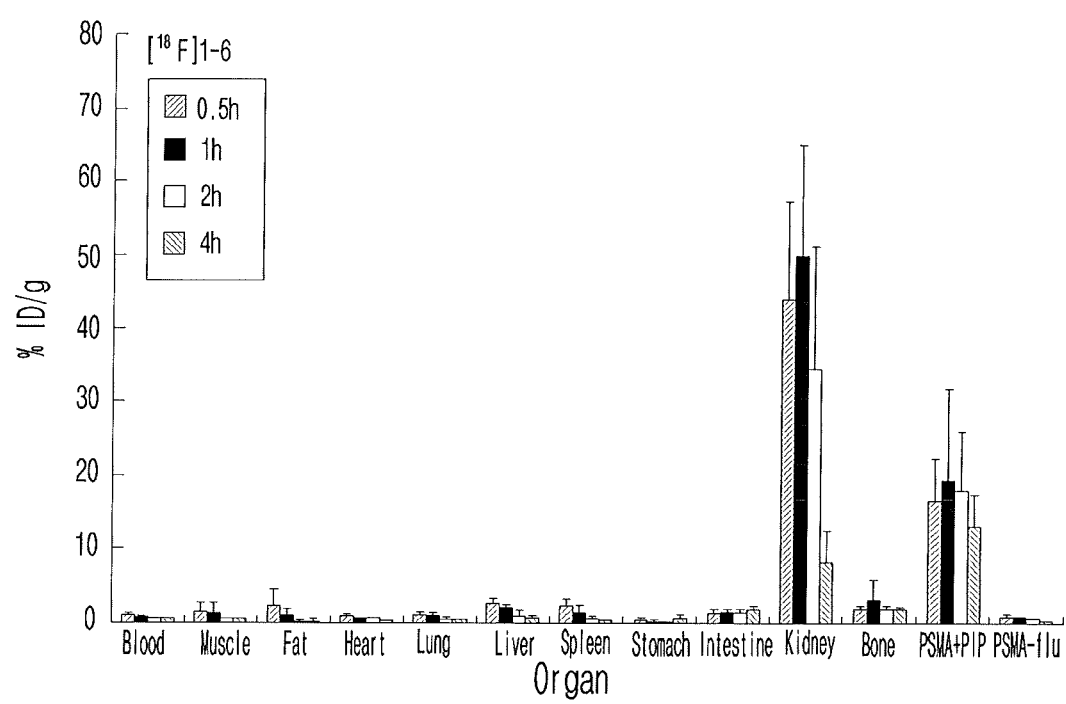

Table 3 and Table 4 show the radioactivity degree of the compounds of Example 7-3 and Example 7-6 in each organ. FIGS. 5A and 5B are graphs illustrating the organ biodistribution over the time.

As a result, as shown in Tables 3 and 4 and FIGS. 5A and 5B, the tumor intake rate (% ID/g) was increased to more than 10%, 30 minutes after the injection of the compounds of Examples 7-3 and 7-6. In addition, the compound of Example 7-3 was confirmed to have higher PSMA-tumor tissue (PC-3 flu) intake rate compared to PSMA+ tumor (PC-3 PIP) and superior normal tissue intake rate compared to tumor.

TABLE 3

| Time (h) | PIP/flu | PIP to muscle | PIP to blood | PIP to spleen | PIP to liver |
| --- | --- | --- | --- | --- | --- |
| 0.5 | 40.59 ± 9.85 | 47.39 ± 38.05 | 35.64 ± 25.01 | 7.74 ± 6.03 | 17.35 ± 4.34 |
| 1 | 103.45 ± 9.73 | 86.15 ± 29.07 | 98.69 ± 30.64 | 13.77 ± 5.53 | 15.92 ± 1.95 |
| 2 | 176.33 ± 65.83 | 334.14 ± 260.49 | 487.24 ± 354.87 | 58.80 ± 53.63 | 18.47 ± 7.63 |
| 4 | 232.60 ± 71.80 | 533.90 ± 188.93 | 766.82 ± 331.65 | 128.24 ± 95.38 | 20.93 ± 7.40 |

TABLE 4

| Time (h) | PIP/flu | PIP to muscle | PIP to blood | PIP to spleen | PIP to liver |
| --- | --- | --- | --- | --- | --- |
| 0.5 | 16.00 ± 5.68 | 13.00 ± 4.97 | 14.05 ± 3.61 | 7.31 ± 3.34 | 5.64 ± 6.10 |
| 1 | 23.08 ± 14.91 | 20.11 ± 14.99 | 30.30 ± 17.05 | 12.46 ± 16.18 | 9.93 ± 13.26 |
| 2 | 33.32 ± 14.64 | 38.11 ± 14.83 | 36.90 ± 9.52 | 25.98 ± 8.66 | 13.71 ± 12.60 |
| 4 | 35.69 ± 11.64 | 45.39 ± 22.54 | 42.90 ± 18.49 | 32.51 ± 10.12 | 19.77 ± 11.81 |

The present invention has been described in detail according to the above embodiments. However, the present invention is not limited by the above embodiments and can be variously modified without departing from the scope of the invention.

What is claimed is:

1. A compound represented by the following formula 1:

[Formula 1]

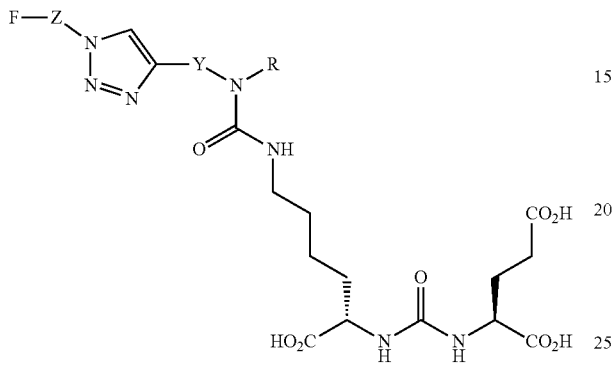

wherein,
Y is $C_1$-$C_5$ alkylene;
Z is —$CH_2$—($CH_2$—O—$CH_2$)$_n$—$CH_2$—, wherein n is an integer of 0 to 5;
R is hydrogen or $C_1$-$C_2$ alkyl having a substituent, wherein the substituent is $C_6$-$C_{12}$ aryl or $C_4$-$C_{10}$ heteroaryl containing one or more elements selected from the group consisting of O, S and N; and
F is $^{18}F$ or $^{19}F$.

2. The compound according to claim 1, wherein Y is $C_1$-$C_2$ alklylene and F is $^{18}F$.

3. A compound represented by A the following formula 11:

[Formula 11]

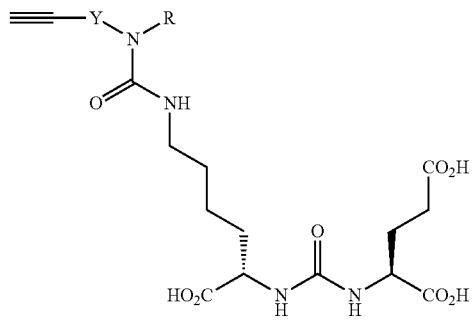

wherein,
Y is $C_1$-$C_5$ alkylene; and
R is hydrogen or $C_1$-$C_2$ alkyl having a substituent, wherein the substituent is $C_6$-$C_{12}$ aryl or $C_4$-$C_{10}$ heteroaryl containing one or more elements selected from the group consisting of O, S and N.

4. The compound according to claim 3, wherein Y is $C_1$-$C_2$ alkylene.

5. A pharmaceutical composition for treating or diagnosing prostate cancer comprising a compound of claim 1 or a pharmaceutically acceptable salt thereof as an active ingredient.

6. A radiopharmaceutical for imaging diagnosis of prostate cancer comprising a compound of claim 1 or a pharmaceutically acceptable salt thereof as an active ingredient.

7. The radiopharmaceutical according to claim 6, wherein the imaging diagnosis includes magnetic resonance imaging (MRI) or positron emission tomography (PET).

8. A method for treating or diagnosing prostate cancer in a subject, said method comprising administering to the subject the pharmaceutical composition of claim 5.

9. A method for diagnostically imaging prostate cancer in a subject, said method comprising administering to the subject the radiopharmaceutical of claim 6.

* * * * *